(12) United States Patent
Naruse et al.

(10) Patent No.: US 9,896,563 B2
(45) Date of Patent: Feb. 20, 2018

(54) PROCESS FOR PRODUCING SPONGELIKE STRUCTURE

(71) Applicant: Toray Industries, Inc., Tokyo (JP)

(72) Inventors: Yoshihiro Naruse, Nagoya (JP); Satoshi Kondo, Kamakura (JP); Shuichi Nonaka, Otsu (JP); Keishi Miwa, Otsu (JP); KaKuji Murakami, Otsu (JP)

(73) Assignee: Toray Industries, Inc., Tokyo (JP)

( * ) Notice: Subject to any disclaimer, the term of this patent is extended or adjusted under 35 U.S.C. 154(b) by 45 days.

(21) Appl. No.: 14/866,367

(22) Filed: Sep. 25, 2015

(65) Prior Publication Data

US 2016/0017112 A1    Jan. 21, 2016

Related U.S. Application Data

(62) Division of application No. 11/990,199, filed as application No. PCT/JP2006/315569 on Aug. 7, 2006, now abandoned.

(30) Foreign Application Priority Data

Aug. 10, 2005  (JP) ................................. 2005-231679
Aug. 19, 2005  (JP) ................................. 2005-238325

(51) Int. Cl.

| C08J 9/36 | (2006.01) |
|---|---|
| C08J 9/28 | (2006.01) |
| A61K 8/02 | (2006.01) |
| A61Q 19/00 | (2006.01) |
| D21H 13/10 | (2006.01) |
| A61Q 1/12 | (2006.01) |
| A61Q 19/08 | (2006.01) |

(52) U.S. Cl.
CPC ............... *C08J 9/36* (2013.01); *A61K 8/02* (2013.01); *A61K 8/0208* (2013.01); *A61Q 1/12* (2013.01); *A61Q 19/00* (2013.01); *C08J 9/28* (2013.01); *D21H 13/10* (2013.01); *A61Q 19/08* (2013.01); *C08J 2323/12* (2013.01); *C08J 2367/03* (2013.01); *C08J 2377/02* (2013.01); *C08J 2381/04* (2013.01); *Y10T 428/298* (2015.01)

(58) Field of Classification Search
None
See application file for complete search history.

(56) References Cited

U.S. PATENT DOCUMENTS

| 3,287,324 A * | 11/1966 | Sweeny ................. C08G 69/32 188/251 A |
| 3,759,775 A | 9/1973 | Shepherd ........................ 156/78 |
| 4,755,335 A * | 7/1988 | Ghorashi ............... D01D 10/00 264/129 |
| 5,429,745 A | 7/1995 | Ogata et al. ............. 210/497.01 |
| 5,472,665 A * | 12/1995 | Rosofsky ................ A61F 13/00 422/27 |
| 2003/0165740 A1 | 9/2003 | Edwards et al. .............. 429/232 |
| 2004/0037813 A1 | 2/2004 | Simpson et al. ............. 424/93.7 |
| 2004/0092185 A1 | 5/2004 | Grafe et al. .................... 442/153 |
| 2004/0126405 A1 | 7/2004 | Sahatjian et al. ............. 424/423 |
| 2004/0241436 A1 | 12/2004 | Hsieh et al. .................. 428/361 |
| 2005/0095695 A1* | 5/2005 | Shindler .................. B82Y 5/00 435/285.1 |

FOREIGN PATENT DOCUMENTS

| EP | 0 042 253 A1 | 12/1981 | |
| EP | 1 564 315 A1 | 8/2005 | |
| GB | 2 178 447 A | 2/1987 | |
| JP | 62-122586 A | 6/1987 | |
| JP | 62-502936 A | 11/1987 | |
| JP | 02-291260 A | 12/1990 | |
| JP | 07-299876 A | 11/1995 | |
| JP | 09-019580 A | 1/1997 | |
| JP | 09-132601 A | 5/1997 | |
| JP | 09-263857 A | 10/1997 | |
| JP | 2001-146630 A | 5/2001 | |
| JP | 2003-265593 A | 9/2003 | |
| JP | 2004-359936 A | 12/2004 | |
| WO | 86/05811 | 10/1986 | |
| WO | WO 86/05811 A1 * | 10/1986 | ............. C12P 21/00 |
| WO | 2005/040495 A1 | 5/2005 | |

OTHER PUBLICATIONS

Kristoff, S. ( eHow.com, What is a Thermoplastic Polymer? Oct. 13, 2011)), "Kristoff".*
Liu et al. (J. Mater. Res. Dec. 2002 17(12): 3206-3211).*
Wan-Ju Li et al., "Multilineage differentiation of human mesenchymal stem cells in a three-dimensional nanofibrous scaffold", Biomaterials 26, pp. 5158-5166 (2005).
Zuwei Ma, Ph.D., et al. "Grafting of Gelatin on Electrospun Poly(caprolactone) Nanofibers to Improve Endothelial Cell Spreading and Proliferation and to Control Cell Orientation" Tissue Engineering vol. 11, No. 7/8, pp. 1149-1158 (2005).
Communication pursuant to Article 94(3) EPC dated Mar. 24, 2010, in Application No. 06 782 411.0-2124.

(Continued)

*Primary Examiner* — Peter J Reddig
(74) *Attorney, Agent, or Firm* — Kubovcik & Kubovcik

(57) ABSTRACT

A spongelike structure or a powder having fibers three-dimensionally arranged therein with high dispersibility, whose apparent density can be designed depending on the purpose or utility, as well as a process producing it. A fiber dispersion in which fibers having a number mean diameter in a predetermined range are dispersed in a dispersion medium, and this fiber dispersion is dried to remove the dispersion medium, thereby, a spongelike structure and a powder are produced.

7 Claims, 6 Drawing Sheets

(56) References Cited

OTHER PUBLICATIONS

Office Action dated Mar. 23, 2011, in Chinese Patent Application No. 200680028920.8 (with partial English translation).
Kristoff, S. (eHow.com, What is a Thermoplastic Polymer? Oct. 13, 2011).
Yahoo! Education (enzyme http://education.yahoo.com/reference/dictionary/enty/enzyme, Oct. 13, 2011).
D. Kopitar et al. (Journal of Fiber Bioengineering and Informatics 6:1 (2013), pp. 103-115).

\* cited by examiner

[Fig. 1]
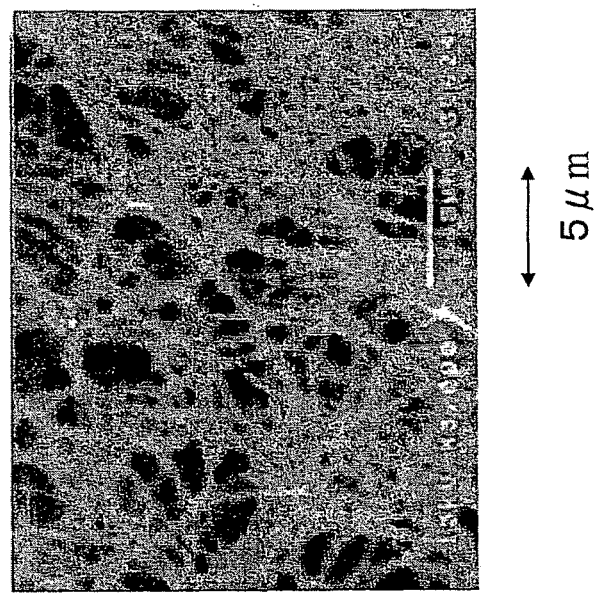

[Fig.2]
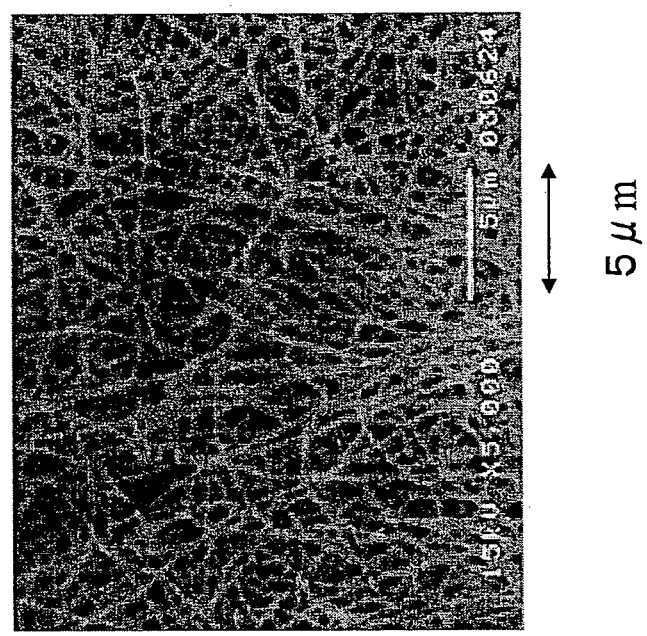

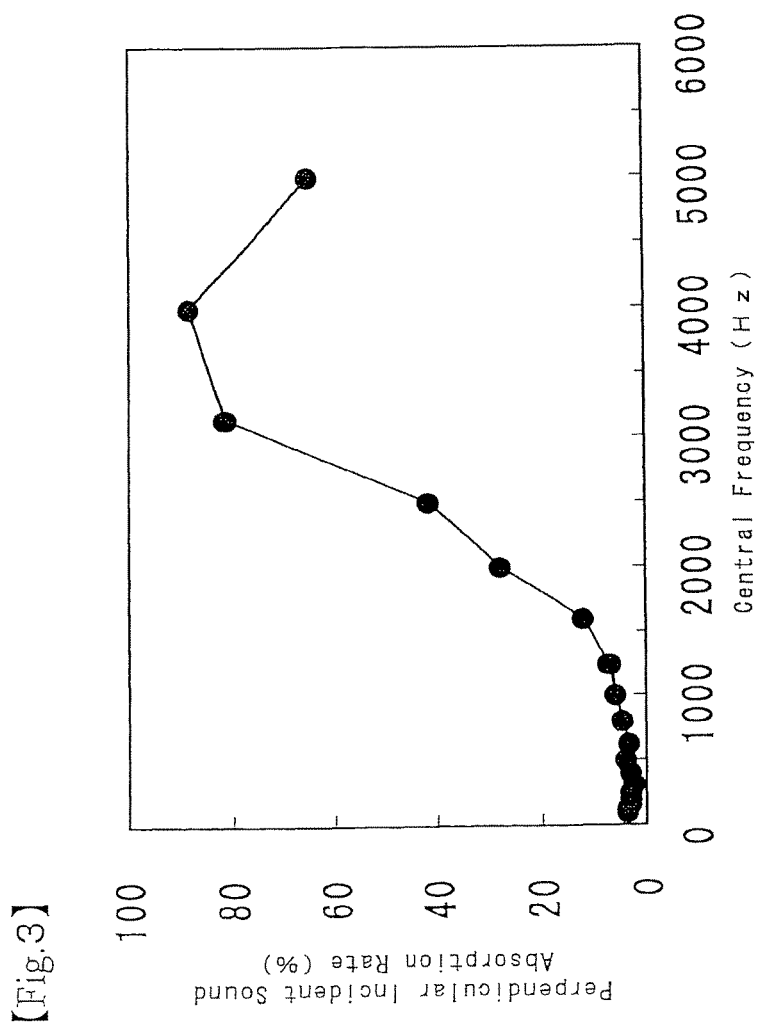
[Fig.3]

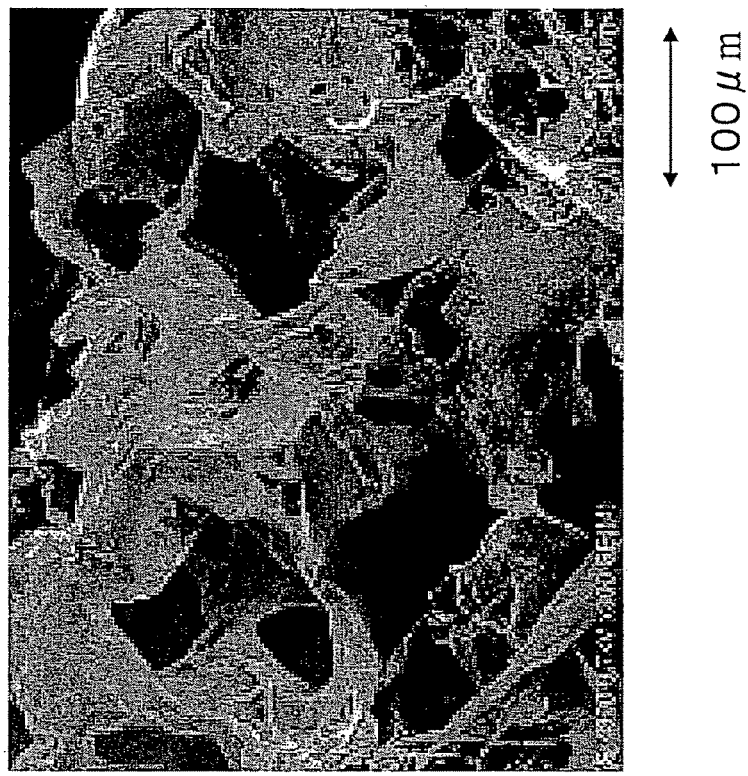
[Fig.4]

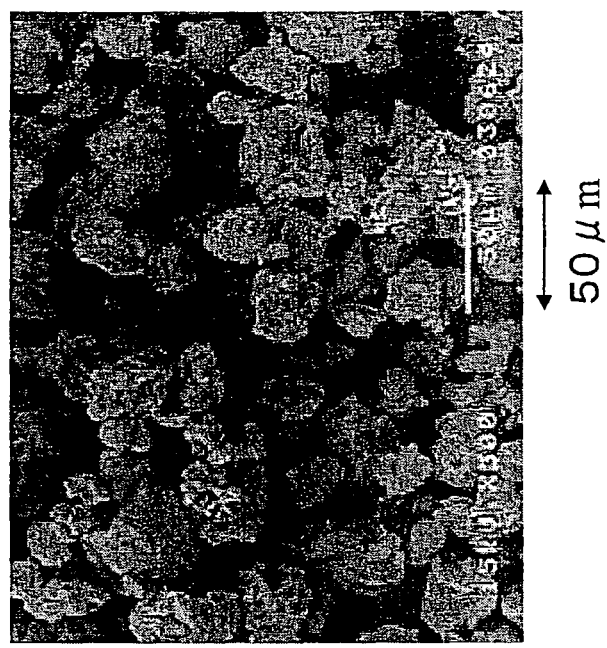
[Fig.5]

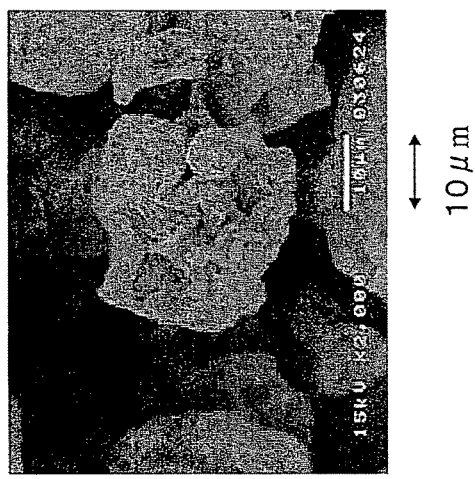
[Fig.6]

PROCESS FOR PRODUCING SPONGELIKE STRUCTURE

This application is a division of application Ser. No. 11/990,199 filed Oct. 31, 2008, now abandoned which is a 371 of International Patent Application No. PCT/JP2006/315569, filed Aug. 7, 2006, and which claims priority based on Japanese Patent Application No. 2005-231679, filed Aug. 10, 2005, and Japanese Patent Application No. 2005-238325, filed Aug. 19, 2005; each of said prior applications being incorporated herein by reference.

TECHNICAL FIELD

The present invention relates to a spongelike structure or a spherical powder in which a fiber is dispersed and arranged three-dimensionally, and a process for producing the same.

BACKGROUND ART

Previously, as a spongelike structure, a variety of moldings are known. For example, there is a molding obtained by mixing a polymer with a blowing agent, placing this into a molding box, and heating to expand this. Specifically, there are expanded foams consisting of urethane, polyolefin or melamine resin. In addition, there are moldings obtained by blending a dissolution material in a polymer, and dissolving out this to form micro pores.

Since the structure obtained by the aforementioned procedure has high porosity, it is widely utilized as a heat insulator, an acoustic material, an adsorbent, a cushioning material or a filter.

Further, in addition to the expanded foams, a spongelike structure obtained by arranging fibers three-dimensionally is also known. Examples of the structure include a structure in which a crimped fiber is formed into a beam structure, and intersecting points of fibers are adhered (see Patent Publication 1).

However, although such the structure has a low apparent density, it is not easy to change a filling density of a fiber in a molding box since fibers are thermally adhered in the state where they are filled into a molding box in order to perform molding, and there is a limit for freely controlling an apparent density. Further, in applications utilizing a specific surface area of a fiber, a smaller number mean diameter of a fiber is required, and as there is the description to the effect that, when a fineness of a single filament is less than 0.5 denier (less than 7 μm in terms of PET specific gravity), bulkiness of the spongelike structure is reduced, in a paragraph [0011] in the Patent Publication, it is difficult to reduce an apparent density in the spongelike structure having a smaller fiber diameter.

For this reason, a spongelike structure in which a fiber diameter is small, an apparent density can be designed depending on an object and an application, and fibers are arranged three-dimensionally, is required.

Additionally, in the field of cell therapy and regenerative medicine, in order to transplant and study a cell, a tissue or an organ, a material which is to be a scaffold for cell cultivating in which a cell is effectively cultivated in vitro, and a material which is to be a scaffold for promoting regeneration or reconstruction of a tissue in vivo (hereinafter, these are collectively referred to as cell culture scaffold) are required. Such the cell culture scaffold material can satisfy various requirements for attaining the aforementioned object, by mimicking the cell environment surrounding a cell.

Meanwhile, in bone marrow or a basement membrane which is one kind of the cell environment surrounding a cell, a cell is grown and proliferated in a three-dimensional matrix called extracellular matrix, such as collagen, constructed of a fibrous structure at a nano-level. For this reason, when a cell is cultivated in vitro for the aforementioned object, previously, a matrix component such as collagen extracted from a living body has been processed into a gel or spongelike structure, and study of this to adopt as a scaffold for three-dimensional cultivating has been progressed (see Patent Publication 2).

However, there are a problem that a biomaterial consisting mainly of a protein can not stand severe treatment, a representative of which is sterile treatment such as autoclave and γ-ray, which is frequently performed in a process for manufacturing a medical material, a problem on stability for long term storage until use, and a problem on a dynamical strength and shape stability. In addition, since a biomaterial such as collagen is generally extracted from an animal such as a cow and a pig, there is a risk that a known or unknown infectious material from these animals, a representative of which is a virus and a prion, is mixed in, and this was a problem upon use as a scaffold material for cultivating a cell in vivo and in vitro, particularly, upon use in medical utility.

For this reason, recently, study of manufacturing a foam or a fibrous material such as a non-woven fabric and a woven fabric using a synthetic polymer in place of a material extracted form a living body, and using them as a three-dimensional cultivating scaffold is being proceeded (see Patent Publication 3-Patent Publication 6).

However, these previous three-dimensional cultivating scaffolds using a synthetic polymer as a material have not an actual shape of a fibrous material called extracellular matrix surrounding a cell in vivo, a representative of which is collagen, particularly a structure mimicking a structure consisting of a fiber at a nano-level. For this reason, they can not be said to mimic the in vivo environment truly, are inferior in affinity for a cell, and influence due to inability to express the cell function as in vivo on the previous scaffold is concerned.

Therefore, in recent years, a structure constructed of a fiber having a diameter at a nano-level (nano-fiber) is paid an attention as a cell scaffold material. For example, many trials to obtain a structure of a nano fiber by a method of blowing a fiber while applying a high voltage, called electrospinning, and cultivating a functional cell, a stem cell or an ES cell used in cell therapy or regenerated medicine on the structure while the function is retained and promoted are performed, and some effect is obtained (see Non-Patent Publications 1 and 2).

However, the structure obtained by such the electrospinning has a defect for use in a scaffold material for cultivating a cell, such as weakness of a fiber strength, ununiformity and scatter of a fiber diameter, and use of an organic solvent upon manufacturing. In addition, since a special process called electrospinning as described above is used, a shape of the resulting structure is limited to a so-called paper-like non-woven fabric structure. For this reason, since the structure as it is has low porosity, and a cell can not enter the interior of a structure, a cell can be cultivated only on a superficial layer, and a cell can not be cultivated three-dimensionally. That is, it is substantially impossible to cultivate a cell at a high density, and it is also impossible to regenerate and reconstruct an organ or a tissue having a thickness in vitro. Further, a non-woven fabric structure also has a defect that a three-dimensional environment in a living body such as bone marrow in which a cell is grown can not be truly reproduced from a view point of a shape.

For this reason, particularly from a view point that a cell or a culture medium can enter the interior of the structure to retain a cell three-dimensionally, and a porous structure and high porosity for passage of a culture medium are possessed, or from a view point of similarity to bone marrow in which many stem cells and hematopoietic cells are grown, as a cell scaffold material for cultivating a cell, a cell scaffold material comprising a spongelike structure consisting of a nanofiber made of a fibrous material, particularly a synthetic material is sought.

Meanwhile, utilization of a fiber not only as the aforementioned spongelike structure, but also as a filler for a resin, a paint and a cosmetic is progressed. Examples of molding of a fiber into a powder include a fine powder obtained by cutting an ultramicrofiber having a diameter of not more than 3 μm into a length of 5 to 100 μm (see Patent Publication 7). However, since this fiber fine powder is merely dispersion of a fiber into a powder, and is obtained by mechanically grinding an ultramicrofiber after freezing, a fiber is randomly ground and cut in a diameter direction and in a longitudinal direction upon freezing and grinding, and a scatter is great in a fiber length from a view point of a powder. For this reason, there is a problem that, when added as filler for a resin, a paint and a cosmetic, dispersity is inferior due to fibers aggregation and its settlement, storage stability is reduced, and when these are coated, uniform coating is difficult.

For this reason, a powder consisting of a fiber, which is excellent in dispersity and storage stability, and is useful as various fillers is also sought.
Patent Publication 1: Japanese Patent Application Laid-Open (JP-A) No. 9-19580
Patent Publication 2: JP-A No. 62-502936
Patent Publication 3: JP-A No. 62-122586
Patent Publication 4: JP-A No. 2-291260
Patent Publication 5: JP-A No. 7-299876
Patent Publication 6: JP-A No. 2003-265593
Patent Publication 7: JP-A No. 2001-146630
Non-Patent Publication 1: Biomaterials 26 p 5158 (2005)
Non-Patent Publication 2: Tissue Eng. 11 p 1149 (2005)

DISCLOSURE OF THE INVENTION

Problems to be Solved by the Invention

An object of the present invention is to provide a spongelike structure in which an apparent density can be designed depending on the purpose and application, and fibers are three-dimensionally arranged.

Another object of the present invention is to provide a spongelike structure suitable as a scaffold for a cultivating a cell, specifically, a spongelike structure which can three-dimensionally hold a cell or a culture medium in the interior thereof, and mimics the environment in a living body surrounding a cell.

A further object of the present invention is to provide a powder consisting of a fiber, which is excellent in dispersity and storage stability.

Mean to Solve the Problems

In order to solve the aforementioned problems, the present invention futures the following:
(1) A spongelike structure in which a fiber having a number mean diameter of 1 nm to 50 μm is fixed in the dispersed state.
(2) The spongelike structure according to (1), wherein the fiber comprises a thermoplastic polymer.
(3) The spongelike structure according to (1) or (2), wherein a number mean diameter of the fiber is 1 to 500 nm.
(4) The spongelike structure according to any one of (1) to (3), wherein a apparent density is 0.0001 to 0.5 g/cm$^3$.
(5) The spongelike structure according to any one of (1) to (4), wherein a number mean size of a micropore constituted by the fiber is not more than 100 μm.
(6) The spongelike structure according to any one of (1) to (5), wherein the fibers are partially adhered.
(7) A heat insulator comprising the spongelike structure as defined in any one of (1) to (6).
(8) An acoustic material comprising the spongelike structure as defined in any one of (1) to (6).
(9) A cell scaffold material comprising the spongelike structure as defined in any one of (1) to (6).
(10) The cell scaffold material according to (9), wherein a number mean size of a macropore present in the spongelike structure is 10 μm to 500 μm.
(11) The cell scaffold material according to (9) or (10), wherein a functional material is adsorbed and/or fixed on a surface of the fiber.
(12) The cell scaffold material according to (11), wherein the functional material is a protein.
(13) A process for producing a spongelike structure, comprising drying a fiber dispersion in which a fiber having a number mean diameter of 1 nm to 50 μm is dispersed in dispersion media, and removing the dispersion media.
(14) The process for producing a spongelike structure according to (13), wherein a number mean diameter of the fiber is 1 to 500 nm.
(15) The process for producing a spongelike structure according to (14), wherein a fiber constituent ratio of single fibers having a diameter of more than 500 nm is not more than 3% by weight.
(16) The process for manufacturing a spongelike structure according to any one of (13) to (15), wherein the fiber comprises a thermoplastic polymer.
(17) The process for producing a spongelike structure according to any one of (13) to (16), wherein a cut fiber length of the fiber is 0.2 mm to 30 mm.
(18) The process for producing a spongelike structure according to any one of (13) to (17), wherein the drying is freeze drying.
(19) The process for producing a spongelike structure according to (18), wherein a freezing temperature upon freeze drying not lower than −80° C. and not higher than −20° C.
(20) The process for producing a spongelike structure according to any one of (13) to (19), wherein pressurized steam treatment is further performed after removal of dispersion media.
(21) A powder comprising a fiber having a number mean diameter of 1 to 500 nm, wherein a number mean size of the powder is 1 to 1000 μm.
(22) The powder according to (21), wherein the fiber comprises a thermoplastic polymer.
(23) The powder according to (21) or (22), wherein the fibers are partially adhered.
(24) A paint comprising the powder as defined in any one of (21) to (23).
(25) A cosmetic comprising the powder as defined in any one of (21) to (23).
(26) A process for producing a powder, comprising granulating and drying a fiber dispersion in which a fiber having a number mean diameter 1 to 500 nm is dispersed in dispersion media, to remove the dispersion media.

(27) The process for producing a powder according to (26), wherein the fiber dispersion is granulated and dried by spray drying.

(28) The process for producing a powder according (26) or (27), wherein the fiber comprises a thermoplastic polymer.

(29) The process for producing a powder according to any one (26) to (28), wherein the fiber is such that a fiber constituent ratio of single fibers having a diameter more than 500 nm is not more than 3% by weight.

(30) The process for producing a powder according to any one of (26) to (29), wherein pressurized steam treatment is further performed after removal of the dispersion media.

Effect of the Invention

According to the present invention, a spongelike structure having a small apparent density and high porosity can be obtained. For this reason, the spongelike structure can be widely used in industrial material field and household wares field such as a light reflector used in a liquid crystal, an adsorbent, a cushioning material, and a water retention material in addition to a heat insulator, an acoustic material, and a cell scaffold material, utilizing such the property. In addition, since the spongelike structure has a micropore of a network structure, it can be utilized as various filters not only for household wares and industrial material but also for medicine. Further, the spongelike structure can be widely used in each field of esthetics, medical service, hygiene and the like.

When the spongelike structure of the present invention is used as a cell scaffold material, a cell scaffold material which can retain a cell and a culture medium in the interior of the structure and which has such a high porosity that a culture medium can be passed therethrough can be obtained. For this reason, a cell can be cultivated at a high density. Further, since the cell scaffold material of the present invention has a particularly high specific surface area, there is the effect that, by controlling a surface nature of the spongelike structure constituting a cell scaffold material by various treatments, it becomes possible to adsorb and carry a functional substance having a function on a cell, a representative which is a protein such as cytokine, on a fiber surface at a high density, and effective cultivating can be performed. At the same time, since the spongelike structure is similar to an extracellular matrix which is a fibrous material at a nano-level, a representative of which is collagen, surrounding a cell in bone marrow, basement membrane and amnion in which many functional cells such as stem cells, hematopoietic cells and mesenchymal cells are grown in a living body, these functional cells which have been previously difficult to be cultivated can be cultivated while the function is retained or promoted. For this reason, it becomes possible to apply the spongelike structure to the field of medical service, diagnosis, research and analysis related to cell culture or tissue regeneration using these cells, particularly the medical field such as regenerative medicine and cell therapy.

Further, according to the present invention, a powder of a granular structure having a constituent fiber of a small diameter and a small apparent can be obtained. For this reason, the powder utilizing such the property can be widely used not only as a filler for a resin, a paint and a cosmetic but also as an adsorbent or a water retention agent and, further in each field of medical service, and hygiene.

In addition, according to each process of the present invention, in all cases, since an apparent density can be easily designed and changed depending on the object and utility, various spongelike structures and powders can be obtained.

BEST MODE FOR CARRYING OUT THE INVENTION

Details of the sponge like structure and the powder consisting of an ultramicrofiber of the present invention, together with desirable aspects will be explained below.

First, the spongelike structure of the present invention is a structure having micropores in the interior of a three-dimensional structure. For this reason, this structure has the action that, when immersed in a liquid, the interior of micropores is substituted with the liquid, and the liquid is absorbed. A three-dimensional shape may be any shape such as a cube, a cuboid, a cylinder, a sphere and a cone.

In the present invention, the spongelike structure is such that fibers having a number mean diameter of 1 nm to 50 μm are fixed in the dispersed state.

Herein, the "dispersed state" refers to a form in which fibers are dispersed, specifically, the state where single fibers are not substantially aggregated. Substantially refers to the case where single fibers are completely random and are not oriented, or the case where fibers are partially bound but almost of them are random and in the non-oriented state, and may be the state where almost of single fibers do not form a bundle. Therefore, the dispersed state is different from an oriented aggregate described in JP-A No. 2004-162244. Hereinafter, a form in which fibers are dispersed is referred to as fiber dispersion in some cases. A SEM photograph of the spongelike structure in which fibers are fixed in the dispersed state obtained in Example 1 below is shown in FIG. 1 and FIG. 2 as one example.

In the present invention, the fiber dispersion is such that a fiber length and a cross-sectional shape of a fiber constituting it are not particularly limited, but it is important that a number mean diameter of fiber (substantially single fiber) is 1 nm to 50 μm. Since by adapting a number mean diameter of fiber in such a range, fibers are easily dispersed in dispersion media in a production step, fibers are easily present uniformly in the spongelike structure without partial uneven presence, and an isotropic spongelike structure can be obtained. In addition, since fibers are easily dispersed in dispersion media, a difference between individuals becomes smaller also when formed into the spongelike structure.

A number mean diameter fiber is preferably 1 nm to 10 μm, further 1 to 1000 nm, more preferably 1 to 500 nm, further preferably 1 to 200 nm, particularly preferably 1 to 100 nm. By reducing the diameter in this range, it becomes easy to control the dispersed state of a fiber in the structure as described later. Hereinafter, particularly, a fiber having a number mean diameter of not more than 1000 nm is called nano-fiber in some cases.

In the present invention, a number mean diameter of the fiber can be obtained as follows: That is, a surface of the spongelike structure is observed with a scanning electron microscope (SEM) at such magnification that at least not less than 150 single fibers can be observed in one field and, letting a fiber width in a direction perpendicular to a longitudinal direction to be a diameter of a single fiber, a number mean of randomly extracted 150 single fibers is calculated.

The spongelike structure of the present invention has preferably an apparent density $\rho_a$ of 0.0001 to 0.5 g/cm$^3$. By adapting an apparent density in the above range, a structure excellent in lightweight properties, adiabaticity and cushioning properties is obtained, and then it becomes possible to widely use it in the field of a heat insulator, a cushioning material, and an acoustic material. In addition, since a structure which can maintain a space for holding a cell and a culture medium and, at the same time, is excellent also in liquid permeability, gas permeability, impact resistance, moldability, and robustness is obtained, the structure can be suitably used as a scaffold material used in cell culture (hereinafter, referred to as cell scaffold material).

In the present invention, the cell scaffold material refers to all materials used in a cell, or a tissue or an organ in which cells gather in vivo and in vitro, or in a portion contacting with blood, humor or a culture medium containing a cell, in which by contact of a cell with a material on the material or in the material, various cell functions such as cell adhesion, attachment, proliferation, differentiation, activation, ambulation, morphology or settlement are expressed, promoted, suppressed, or maintained. Specifically, examples include a material which is effective in medical service and research, a material which is used as a part or all of a container, a bag, and a column for cultivating and forming a cell tissue, a transplanting tissue and a transplanting organ, a material which is used as a part or all of an artificial organ and an artificial tissue such as an artificial bone, an artificial heart, an artificial blood vessel, an artificial cornea, an artificial skin, and an artificial nerve, a material which is used as a part of all of a utensil and an instrument used in operation and treatment such as a suture and a template for fracture, and a material which is used as a part or all of a medical equipment used for curing a disease and a wound such as a syringe, a catheter, a wound dressing and an adhesion preventing agent.

As a structure of such the cell scaffold material, in order to cultivate or grow a cell at a high density, it is preferable that the structure has a macropore so that a cell enters the interior, is retained and can be proliferated and differentiated, or has a high porosity in order to retain or circulate a culture medium in the interior. From such a view point, the spongelike structure of the present invention can be used as a cell scaffold material. According to the spongelike structure of the present invention, a space for retaining a cell or a culture medium can be maintained and, further, a culture medium can flow in a macropore or between fibers.

An apparent density is more preferably 0.001 to 0.1 g/cm$^3$, further preferably 0.01 to 0.05 g/cm$^3$. Particularly, when the spongelike structure of the present invention is used as a cell scaffold material, from a view point of the cell or culture medium retaining performance or liquid permeability, an apparent density is more preferably 0.0005 to 0.02 g/cm$^3$, further preferably 0.001 to 0.01 g/cm$^3$.

In the present invention, an apparent density $\rho_a$ (g/cm$^3$) can be obtained as follows: That is, the spongelike structure is excised into a shape such as a cube and a cuboid, a size of each side is measured using a ruler or a slide caliper, a volume of the spongelike structure is obtained and this is designated as V (cm$^3$). In addition, a weight of the excised spongelike structure is measured, and this is designated as W (g). By dividing W by V, an apparent density $\rho_a$ can be obtained.

The spongelike structure of the present invention has preferably a porosity $F_V$ of not lower than 80%. By adopting a porosity in the aforementioned range, the structure contains many air layers, and then a structure excellent in adiabaticity, acoustic absorbability and the like is obtained; also, it becomes possible to widely use the spongelike structure in the industrial material field such as a heat insulator and an acoustic material. In addition, by adopting a porosity in the above range, many spaces are contained in the structure, and then a cell becomes easy to enter the interior; also, the ability of retaining a cell culture medium is increased. Further, the structure excellent also in liquid permeability, gas permeability and heat-retention is obtained. Therefore, the spongelike structure can be suitably used as a scaffold material used in cell culture.

A porosity is more preferably not lower than 90%, further preferably not lower than 95%. An upper limit of a porosity is more preferably not higher than 99.95%, further preferably not higher than 99.9%.

In the present invention, a porosity $F_V$ (%) can be obtained as follows: that is, using a volume V (cm$^3$) and W (g) used when the aforementioned apparent density is obtained and, further, using a specific gravity $S_g$ (g/cm$^3$) of a fiber forming the spongelike structure, the porosity is obtained by the following (1) equation.

$$F_V(\%)=(W/S_g)/V \times 100 \quad (1)$$

Thereupon, when a component other than a fiber, for example, an additive or the like is contained, a porosity may be obtained considering also a density and a weight of the additive, for example, using the following (2) equation; further, even when a plurality of additives are contained, a porosity can be obtained under the similar consideration.

$$Fv(\%)=((W_f/S_f)+(W_r/S_r))/V \times 100 \quad (2)$$

Wherein, $W_f$: a weight of fiber, $S_f$: a specific gravity of a fiber, $W_r$: a weight of an additive, $S_r$: a specific gravity of an additive Examples of a fiber constituting the spongelike structure of the present invention include a natural fiber such as cellulose made of wood pulp, cotton, hemp, wool and silk, a regenerated fiber such as rayon, a semi-synthetic fiber such as acetate, and a synthetic fiber, a representative of which is nylon, polyester and acryl; the kind of a fiber is not particularly limited, but a fiber obtained from a synthetic polymer is preferable. When a fiber used in the present invention is manufactured from a synthetic polymer, a strength against various treatments, a representative of which is sterile treatment with an autoclave and chemical surface treatment described later, and safety regarding mixing of an unknown infectious substance upon use in medical utility are easily enhanced.

A kind of a synthetic polymer is not particularly limited, but from a view point of easy moldability into a fiber, a thermoplastic polymer is preferable. In the case of a thermoplastic polymer, since a fiber can be manufactured utilizing a melt spinning method, productivity can be considerable enhanced.

Examples of the thermoplastic polymer referred in the present invention include a polyester such as polyethylene terephthalate (hereinafter, referred to as PET in some cases), polytetramethylene terephthalate (hereinafter referred to as PTT in some cases), polybutylene phthalate (hereinafter, referred to as PBT in some cases), polylactic acid (hereinafter, referred to as PLA in some cases) and the like, a polyamide such as nylon 6 (hereinafter, referred to as N6 in some cases), nylon 66 and the like, polystyrene (hereinafter, referred to as PS in some cases), a polyolefin such as polyporopylene (hereinafter, referred to as PP in some cases) and the like, polyphenylene sulfide (hereinafter, referred to as PPS in some cases) and the like. Among them, a polycondensation polymer, a representative of which is a polyester and a polyamide, has a high melting point in many cases, being more preferably. When a melting point of a polymer is not lower than 165° C., heat resistance of a fiber is better, being preferable. For example, the melting point of PLA is 170° C., the melting point of PET is 255° C., and the melting point of N6 is 220° C. And, from a view point of easy melt spinning, a polymer having a melting point of not higher than 300° C. is preferable.

A polymer may contain an additive such as particles, flame-retardant, an antistatic agent and the like. In addition, other component may be copolymerized in such a range that a nature of a polymer is not deteriorated.

In addition, when the spongelike structure of the present invention is used as a cell scaffold material, it is preferable to use a synthetic polymer such as polyamide (nylon), polyurethane, polylactic acid, polyglycolic acid, polyortho ester, polyanhydrides, polymethyl metharylate, polysulfone, polyethylene terephthalate and polypropylene, which have high biocompatibility and have actual results as a medical device such as a scaffold and a template for regenerating and restoring a tissue such as a skin, a paradentium tissue and gnathic bone, a suture for operation, artificial kidney and a contact lens. Inter alia, it is preferable to use a hydrophilic polymer such as a polyamide including nylon and polyurethane in order to impregnate with a culture medium, a humor and blood. On the other hand, in order to strongly adsorb a functional substance having the function on a cell with hydrophobic interaction, it is preferable to use a hydrophobic polymer such as polystyrene.

In the spongelike structure of the present invention, it is preferable that a number mean size of a micropore constructed between single fibers is not larger than 100 µm. By adopting a number mean size of not larger than 100 µm, for example, when the spongelike structure is utilized in a filter, it becomes possible to effectively collect a fine particle and a component which are wanted to be collected. A number mean size of a micropore is more preferably not larger than 10 µm, further preferably not larger than 1 µm. A lower limit of a number mean size is not particularly limited, but is preferably not smaller than 10 nm.

In the present invention, a number mean size of a micropore is obtained as follows: that is, as described in Examples described later, the spongelike structure is observed with SEM, and is digitalized in one field of an observed photograph by image analyze, an area of a pore surrounded by fibers around a surface in an image is measured, and a diameter of a circle equivalent to the pore is obtained from the area value as the a number mean size of the pore.

Further, the spongelike structure of the present invention, when used as a cell scaffold material, has preferable a macropore, and it is preferable that a number mean size of a macropore is 10 µm to 500 µm. A macropore referred herein is a pore surrounded by a wall structure formed by association of fibers as shown in FIG. 4, and refers to a relatively large communicating pore present in the so-called spongelike structure, unlike the aforementioned micropore constructed between single fibers. By adopting a number mean size of a macropore of not larger than 500 µm, upon addition of a cell and a cell culture medium, it becomes possible to effectively capture and retain a cell, cell culture medium and components in a cell culture medium. In addition, since a distance between cells is reduced, interaction by contact between cells is effectively performed, and a spongelike three-dimensional structure of bone marrow can be ideally mimicked. A number mean size of a macropore is more preferably not larger than 300 µm, further preferably not larger than 200 µm. A lower limit of a number mean size of the macropore is preferably not smaller than 10 µm. When a number mean size of a macropore is smaller than 10 µm, a cell becomes difficult to enter a structure, and it also becomes difficult to freely move. In addition, a cell culture medium also becomes difficult to freely pass through the structure, and there is a problem that supply of a nutrient to a cell and discharge of waste products are inhibited, and cell culture and tissue formation are not effectively performed.

In the present invention, a number mean size of a macropore is obtained as follows: that is, the spongelike structure is observed with SEM; in one field of a taken photograph, 50 pores having a diameter of a circle equivalent to the pore of not smaller than 1 µm are arbitrary selected from pores surrounded by a wall structure formed by association of fibers, and a sum of the diameters of a circle equivalent to the pore of 50 pores is simply averaged.

In order to use the spongelike structure of the present invention as a cell scaffold material for cultivating a cell in vitro or promoting the function expression of a cell in vivo in cell therapy or regenerative medicine, it is preferable that a cell scaffold material forms a structure close to the in vivo environment in which a cell is grown in vivo, and it is particularly preferable that a cell scaffold material mimics a structure of bone marrow, basement membrane and amnion in which many cells used in cell therapy and regenerative medicine are present. It is thought that, by mimicking a structure of bone marrow, a cell can be cultivated while the cell maintains the same function as that in a living body, or expresses the same function as that in a living body. In the in vivo environment such as bone marrow, an extracellular matrix such as collagen surrounds a cell, and this extracellular matrix has a shape of a fiber at a nano-level, that is, a shape of a nano-fiber. Further, since this extracellular matrix is aggregated to have a spongelike three-dimensional structure, the spongelike structure of the present invention is used as a cell scaffold material, and so a bone marrow structure can be truly mimicked. As a result, it can be said that the material becomes a suitable culture material for cultivating cells useful in cell therapy or regenerative medicine.

Cell therapy or regenerative medicine is therapy for trying disease treatment, and regeneration and function restoration of a tissue and an organ by cultivating a cell such as a stem cell in vitro, processing this into a tissue and an organ, and transplanting it, or expressing the function of these cells in vivo to promote restoration and regeneration of a tissue and an organ. Herein, a stem cell refers to a cell which is converted into a particular cell when it receives an instruction to change into a cell, that is, has the ability to differentiate, has the ability to become a cell having various functions, and also has the ability to duplicate and regenerate itself over a long term in the undifferentiated state before change is attained.

The spongelike structure of the present invention, when used as a cell scaffold material, is such that a number mean diameter of a constituent fiber is more preferably 1 to 500 nm, further preferably 1 to 200 nm, further preferably 1 to 100 nm, in that the material mimics an extracellular matrix fiber, a representative of which is a collagen fiber present in bone marrow. An extracellular matrix fiber, a representative of which is a collagen fiber, has a bundle shape at a nano-level, and adoption of a number mean diameter of a constituent fiber in the aforementioned range results in more correct mimicking of the shape.

In addition, it is preferable that a functional substance such as cytokine (protein) influencing on control of the cell function is adsorbed onto the cell scaffold material, but when a fiber diameter is made to be small, a specific surface area per volume of the structure is increased to that extent, and absorbability of the functional substance is also improved.

As a result, it becomes possible to present a functional substance to a cell at a high density. Therefore, use of the aforementioned nano-fiber having a fiber diameter at a nano-level is very useful also from a view point of carriage of a substance associated with the cell function at a high density.

Further, when the nano-fiber is used, innumerable spaces of a few nm to a few hundreds nm are formed between fibers in the spongelike structure, and a substance can be retained in this space. Therefore, the excellent absorbing property peculiar in a structure consisting of a nano-fiber, which was not seen in the previous structure consisting of a microfiber, is exhibited. For this reason, when the spongelike structure of the present invention is constructed of a fiber having the aforementioned fiber diameter, and is used as a scaffold material for cell culture and tissue regeneration or as an embedded medical material, a cell culture medium, a humor or blood is absorbed and retained between fibers at a large amount. The retention performance is dramatically improved as compared with the previous cell scaffold material consisting of a microfiber, a preferable nature on operability upon cell culture or upon transplantation of a cultivated cell or tissue is developed, such as not only retention of a large amount of a liquid, but also difficulty in overflow of a liquid from the spongelike structure consisting of a nano-fiber.

In addition, it is enough that a cell scaffold material is entirely or partially constructed of the spongelike structure of the present invention, and it is preferable that at least a part which is to be contact with a cell is constructed of a spongelike structure.

On the other hand, when the spongelike structure of the present invention is used as a heat insulator, in order to exhibit the excellent adiabaticity, it is important that a heat conductivity $\lambda_0$ of such the spongelike structure is not higher than 0.05. In order that a heat conductivity $\lambda_0$ is not higher than 0.05, it is necessary that many immobilized air layers are possessed in the spongelike structure; in the spongelike structure of the present invention, when an apparent density is designed to be not higher than 0.1 g/cm$^3$, the spongelike structure having many fine pores is obtained, and then the structure performs excellent adiabaticity such as a heat conductivity $\lambda_0$ of not higher than 0.05.

A method of measuring a heat conductivity is described in Examples described later in detail, and a heat conductivity is measured according to "Method of measuring thermal resistance and heat conductivity of thermally insulating material-second section: heat flow meter method" described in JIS-A1412-2 (1999). A heat conductivity $\lambda_0$ is preferably not higher than 0.045, more preferably not higher than 0.040.

Although the spongelike structure of the present invention can be used alone as a heat insulator, it can be used in combination with a general heat insulator. Examples of a general heat insulator include foams such as glass wool, polyolefin foam, polystyrene foam, and urethane foam.

In addition, when the spongelike structure of the present invention is used as an acoustic material, in order to exert the excellent sound absorption, it is preferable that a maximum sound absorption rate is not lower than 70% in a frequency of between 100 to 5000 Hz. In order that a sound absorption rate is not lower than 70%, it is necessary that a large amount of the air is contained in the spongelike structure. Due to a viscosity resistance of the air layer, sound is absorbed by converting into a heat energy. In the spongelike structure of the present invention, in order that a sound absorption rate thereof is not lower than 70%, it is required that an apparent density of the spongelike structure is designed to be not higher than 0.1 g/cm$^3$.

A method of measuring a sound abruption rate is described in Examples described later in detail, and a sound absorption rate is measured according to "Method of measuring perpendicular incident sound absorption rate" described in JIS-A1405 (1999).

In addition, although the spongelike structure of the present invention can be used alone as an acoustic material as far as the aforementioned performance is satisfied, it can be also used in combination of a general acoustic material. Examples of the general acoustic material include a non-woven fabric consisting of a natural fiber or a synthetic fiber, and a foam such as glass wool, cellulose, sponge and polyolefin foam.

Further, in order to impart sound absorption characteristics in a lower frequency region, it is also possible to laminate the spongelike structure of the present invention and various films, and utilize membrane oscillation of the film.

Then, a process for producing the aforementioned spongelike structure of the present invention will be explained.

The spongelike structure of the present invention is obtained by preparing a fiber dispersion in which a fiber having a number mean diameter of 1 nm to 50 µm in dispersion media, and drying the fiber dispersion to remove dispersion media.

A number mean diameter of a fiber is preferably 1 nm to 10 µm, further preferably 1 to 1000 nm, more preferably 1 to 500 nm, further preferably 1 to 200 nm, particularly preferably 1 to 100 nm. By reducing the diameter in this range, it becomes easy to disperse a fiber in dispersion media as described later.

A process for producing a fiber used in the present invention is not particularly limited, but the fiber can be obtained by a normal melt spinning method or the like. For example, as one example of a process for obtaining a nano-fiber having a number mean diameter of not larger than 1 µm (1000 nm), that is, a polymer alloy melt containing 2 or more kinds of polymers having different solubilities in a solvent is prepared, and this is spun, and cooled and solidified to form a fiber. If necessary, the fiber is drawn and thermally treated to obtain a polymer alloy fiber. Moreover, a nano-fiber used in the present invention can be obtained by removing an easy soluble polymer with a solvent.

Herein, in a polymer alloy fiber which is a precursor of a nano-fiber, it is important to form a sea (matrix) with an easy soluble polymer, to from an island (domain) with a low soluble polymer and to control the island size. Herein, the island size is such that a transverse cross section of the polymer alloy fiber is observed with a transmission electron microscope (TEM) and is assessed a diameter of a circle equivalent to the fiber. Since a diameter of a nano-fiber is approximately determined by an island size in a precursor, distribution of the island size is designed according to diameter distribution of a nano-fiber. For this reason, kneading of a polymer to be alloyed is very important, and it is preferable to highly knead the polymer with an extruder or a static mixer. In addition, since in a simple chip blending (the method described, for example, in JP-A No. 6-272114, JP-A No. 10-53967 etc.), kneading is deficient, it is difficult to disperse islands at a few tens nm size.

As a measure upon specific kneading, depending on polymers to be combined, when an extruder is used, it is preferable to use a double-screw extruder and, when a static mixer is used, it is preferable that the number of division is not less than one million. In addition, in order to avoid unevenness of blending and variation in a blending ratio with time, it is preferable to weigh respective polymers independently, and supply polymers to a kneading device independently. Thereupon, polymers may be supplied separately as a pellet, or may be supplied in the melt state. Alternatively, two or more kinds of polymers may be supplied to a bottom of an extruder or side feed may be adapted in which one component is supplied midway of an extruder.

When a double-screw extruder is used as a kneading device, it is preferable to balance both of high kneading and suppression of a polymer retention time. A screw is constructed of a feeding part and a kneading part, and by adapting a length of a kneading part of not less than 20% of an effective length of a screw, high kneading can be achieved, being preferable. In addition, by adapting a length of a kneading part of not more than 40% of a screw effective length, an excessive shearing stress can be avoided, and a retention time can be shortened, thereby, thermal deterioration of a polymer and gelling of a polyamide component can be suppressed. By positioning a kneading part on a discharge side of a double-screw extruder if possible, a retention time after kneading can be shortened and reaggregation of an island polymer can be also suppressed. In addition, when kneading is intensified, a screw having the back flow function of feeding a polymer in an extruder in a reverse direction may be provided.

In order to disperse an island super-finely in a few tens nm size, combination of polymers is also important.

In order that an island domain (nano-fiber cross section) approaches a circular shape, it is preferable that an island polymer and a sea polymer are incompatible. However, in the case of simple combination of incompatible polymers, sufficient superfine dispersion of an island polymer is difficult. For this reason, it is preferable to optimize compatibility of polymers to be combined, and one of indices therefor is a solubility parameter (SP value). The SP value is a parameter of reflecting an aggregating force of a substance defined by (evaporation energy/molar volume)$^{1/2}$, and substances having close SP values easily afford a polymer alloy having better compatibility. The SP value is known in various polymers, and is described, for example, in "Plastic Databook" coedited by Asahi Kasei Amidas Corporation/ Plastics Edition Section, page 189. When a difference in SP values of two polymers is 1 to 9 $(MJ/m^3)^{1/2}$, both of circulization and superfine dispersion of an island domain due to incompatibilization are easily balanced, being preferable. For example, a difference in SP value between nylon 6 (N6) and PET is around 6 $(MJ/m^3)^{1/2}$, and this is a preferable example; a difference in SP value between N6 and polyethylene (PE) is around 11 $(MJ/m^3)^{1/2}$, and this is exemplified as a not preferable example.

It is preferable that a difference in a melting point between polymers is not greater than 20° C. since a difference in the melt situation in an extruding kneader hardly occurs, particularly, upon kneading using an extruding kneader and kneading at a high efficiency is easy. When a polymer which is easily thermally degraded or thermally deteriorated is used as one component, it is necessary to suppress a kneading or spinning temperature low, and suppression of a difference in a melting point between polymers at not greater than 20° C. is also advantageous. Herein, since a melting point is not present in the case of an amorphous polymer, a glass transition temperature or a Vicat softening temperature or a deformation temperature is used instead of this.

Further, a molten viscosity is also important. A molten viscosity of a sea polymer greatly influences on spinnability in some cases, and when a low viscosity polymer of not greater than 100 Pa·s is used as a sea polymer, it is easy to disperse an island polymer, being preferable. Thereby, spinnability can be remarkably improved. A molten viscosity is a value at a spinneret temperature and a shearing rate of 1216 sec$^{-1}$ upon spinning.

When a superfinely dispersed polymer alloy is spun, design of a spinneret is important, and the condition for cooling a thread is also important. Since the polymer alloy is a very unstable molten fluid as described above, it is preferable to cool and solidify it rapidly after discharge from a spinneret. For this reason, a distance from a spinneret to cooling initiation is preferably 1 to 15 cm. Herein, cooling initiation means a position at which positive cooling of a thread is initiated; in an actual melt spinning apparatus, an upper end part of a chimney corresponds to this.

By removing an easy soluble polymer of the thus spun a polymer alloy fiber (island-in-sea fiber) with a solvent, a nano-fiber used in the present invention can be obtained.

In a process for producing the nano-fiber, particularly when a static mixer is situated immediately before a spinneret, a filament-shaped nano-fiber in which a nano-fiber is extended indefinitely can be obtained theoretically.

The aforementioned nano-fiber obtained with a polymer alloy is entirely different from a nano-fiber obtained by electrospinning, and a nano-fiber is also drawn and thermally treated by drawing and thermally treating a polymer alloy fiber which is a precursor. For this reason, a tensile strength and a shrinkage rate of the resulting nano-fiber can be freely controlled. In addition, since the fiber is crystallized and oriented by drawing/thermal treatment, a high strength nano-fiber having an equivalent strength to that of a normal fiber for clothing and having a crystallization degree of not lower than 20% can be obtained. Therefore, when the fiber obtained by such the method is used in the spongelike structure of the present invention, it is easy to obtain a suitable structure strength as a spongelike structure, and it becomes easy to form a three-dimensional structure having a variety of designed patterns. The polymer alloy fiber which is a precursor can be further crimping-processed.

Further, when a non-woven fabric consisting of a nano-fiber produced by electrospinning is used in a cell scaffold material, there was a problem that a porosity for retaining a cell or a culture medium is small, form stability is deficient, and a strength and a size (width) themselves are deficient. For example, a cell scaffold material used for in vivo embedding or during circulation cultivating is required to have a product strength and a proper macropore porosity. However, since the nano-fiber produced by electrospinning is a fiber obtained by blowing polymer at a high voltage, a fiber strength itself is weak; there is a possibility that controllability of a micro-structure as a cell scaffold is generally lacked in a non-woven fabric form which can be solely formed by electrospinning, and it is impossible to obtain uniform macropore into which a cell enters. A non-woven fabric using a nano-fiber obtained by electrospinning is weak in a mechanical structure; when applied it to a cell scaffold material, a particular binding material or a backing material is required in some cases in order to maintain structural stability, and there are many limits in use.

To the contrary, when a spongelike structure consisting of a nano-fiber obtained by melt-spinning a polymer alloy is used in a cell scaffold material, the spongelike structure not only has a high porosity for retaining a cell and a culture medium, but also is constructed of an oriented and crystallized high strength nano-fiber, and so various performances required as a cell scaffold material such as form stability and a strength can be attained and it can be said that the structure is suitable in cell culture and tissue regeneration. Particularly, the structure has a micro-structure mimicking the environment such as bone marrow and stroma in a living body, and fine distribution of a functional substance such as cytokine can be achieved, being preferable.

From the above reasons, it is preferable to use a nano-fiber obtained by melt-spinning a polymer alloy in the present invention.

The fiber obtained as described above is cut into a desired fiber length using a cutting machine such as a guillotine cutter, a slice machine, and a cryostat. Since the aforementioned fiber obtained by a melt spinning method is obtained as a fiber bundle in which fibers are aligned in a certain direction, it is possible to adjust all cut fibers at a desired fiber length. Here, in a nano-fiber by an electrospinning method, since a fiber bundle in which fibers are aligned in a certain direction cannot be produced due to its process, a fiber length can not be uniformed even when cut, and so the fiber is not suitable for preparing a fiber dispersion.

In order to improve dispersity of a fiber in a fiber dispersion, when a length of a cut fiber is too great, there is a tendency that dispersity is deteriorated. On the other hand, in the case of a too small length of a cut fiber, when prepared into the spongelike structure, a degree of association or entanglement of a nano-fiber becomes small; as a result, a strength of the structure is reduced. For this reason, it is preferable to cut a fiber at a length of 0.2 to 30 mm. A fiber length is more preferably 0.5 to 10 mm, further preferably 0.8 to 5 mm.

Then, the resulting cut fiber is dispersed in a dispersion medium. As the dispersion medium, not only water, but also a general organic solvent such as a hydrocarbon medium such as hexane and toluene, a halogenated hydrocarbon type solvent such as chloroform and trichloroethylene, an alcohol type solvent such as ethanol, isopropyl alcohol, butyl alcohol and hexanol, an ether type solvent such as ethyl ether, tetrahydrofuran and dioxane, a ketone type solvent such as acetone and methyl ethyl ketone, an ester type solvent such as methyl acetate and ethyl acetate, a polyalcohol type solvent such as ethylene glycol and propylene glycol, and an amine or amide type solvent such as triethylamine and N,N-dimethylformamide can be suitably used also in view of affinity for a fiber. In this regard, when safety and the environment are taken into consideration, it is preferable to use water as the dispersion medium. In addition, from a view point that the spongelike structure is produced by removing the dispersion medium as described later, a dispersion medium having such as a nature that a medium can be sublimed under the ambient pressure or low pressure condition is preferable, and it is preferable to use water also from such the view point. In addition, the dispersion medium can be used alone or in combination of two or more kinds.

As a method of dispersing a cut fiber in a dispersion medium, a stirrer such as a mixer, a homogenizer, an ultrasonic stirrer and the like can be used. In the case of a form in which single fibers in a cut fiber are aggregated firm such as a nano-fiber obtained by a melt spinning method, it is preferable to perform refining in a dispersion medium as a pretreatment step to dispersion by stirring. A shearing force is imparted to a fiber with a Niagara beater, a refiner, a cutter, a laboratory scale grinding machine, a biomixer, a household mixer, a roll mill, a mortar, a PFI mill, a bath type ultrasonic processor or a probe type ultrasonic processor to disperse fibers one by one, and thereafter, fibers are traced into a dispersion medium.

In order to prepare a fiber dispersion, it is necessary that a fiber itself has such the mechanical strength that the fiber can stand various operations; since the aforementioned nano-fiber produced by a melt spinning method can obtain a mechanical strength by orientation and crystallization, it is preferable. The nano-fiber produced by the above production process has a crystallization degree of not lower than 20%, and the fiber becomes to have an equivalent strength to that of a normal fiber for clothing.

When a number mean diameter of a fiber constituting the spongelike structure is in a rage of 1 to 500 nm as described above, it is preferable that a fiber to be dispersed in a dispersion medium is such that a constitutional ratio of a single fiber having a diameter of greater than 500 nm is not more than 3% by weight. Herein, the constitutional ratio of such the bulky fibers means a ratio of a weight of bulky single fibers (having a diameter of greater than 500 nm) relative to a weight of a whole fiber having a diameter of greater than 1 nm, and is calculated as follows. That is, letting a diameter of each single fiber in a fiber bundle to be $d_i$, a square sum $(d_1^2+d_2^2+\ldots+d_n^2)=\Sigma d_i^2(i=1\sim n)$ is calculated. In addition, letting a diameter of each single fiber having a diameter of greater than 500 nm in a fiber bundle to be $D_i$, a square sum $(D_1^2+D_2^2+\ldots+D_m^2)=\Sigma D_i^2(i=1\sim m)$ is calculated. By calculating a ratio of $\Sigma D_i^2$ relative to $\Sigma d_i^2$, an area ratio, that is, a weight ratio of bulky fibers relative to a whole fiber can be obtained.

A constitutional ratio of single fibers having a diameter of greater than 500 nm is more preferably not more than 1% by weight, further preferably not more than 0.1% by weight. That is, this means that the presence of a bulky fiber exceeding 500 nm is near zero.

Further, when a number mean diameter of a single fiber of a fiber bundle is not greater than 200 nm, a constitutional ratio of a single fiber having a diameter of greater than 200 nm is preferably not more than 3% by weight, more preferably not more than 1% by weight, further preferably not more than 0.1% by weight. When a number mean diameter of a single fiber of a fiber bundle is not greater than 100 nm, a constitutional ratio of a single fiber having a diameter of greater than 100 nm is preferably not more than 3% by weight, more preferably not more than 1% by weight, further preferably not more than 0.1% by weight.

Like this, by suppressing a constitutional ratio of bulky fibers in a fiber dispersion using the fiber bundle low, the resulting spongelike structure becomes homogeneous. Also, when plurality of spongelike structures are produced from the same fiber dispersion, a difference between individuals is eliminated, and stability of product quality can be made to be better.

In order to make dispersity of a fiber in a fiber dispersion uniform, or in order to improve a mechanical strength of a structure when prepared into the spongelike structure, a concentration of a fiber in the dispersion is preferably 0.001 to 30% by weight relative to a total weight of the dispersion. In particular, since a mechanical strength of a structure greatly depends on the presence state of a fiber in the dispersion, that is, a distance between fibers, it is preferable to control a concentration of a fiber in the dispersion in the above range. A concentration of a fiber in the dispersion is more preferably 0.01 to 10% by weight, further preferably 0.05 to 5% by weight.

In order to suppress re-aggregation of fibers, improve the surface state of a fiber, improve adherability between fibers, or impart the functionality to a fiber, an additive such as a dispersant may be used in a dispersion, if necessary. As a kind of an additive, there are exemplified a natural polymer, a synthetic polymer, an organic compound and an inorganic compound. Examples of a polymer additive to be added to an aqueous dispersion include an anionic compound such as polycarboxylate, a cationic compound such as a quaternary ammonium salt, and a nonionic compound such as polyoxyethylene ether and polyoxyethylene ester. These can suppress aggregation of fibers to enhance a dispersity. A molecular weight of such the additive for improving a dispersity is preferably 1000 to 50000, more preferably 5000 to 15000.

A concentration of the additive is preferably 0.00001 to 20% by weight, more preferably 0.0001 to 5% by weight, most preferably 0.001 to 1% by weight based on a whole dispersion. Thereby, the sufficient dispersing effect can be obtained.

As an additive which improves adherability between nano-fibers to improve a strength of the structure, there are exemplified reactive polymers and hydrophobic polymers such as those having an amino group, a carboxyl group, an isocyanate group and a hydroxyl group. In addition, an inorganic salt as a substance for forming a pore in the spongelike structure may be added. In addition, a functional substance which is absorbed onto a fiber surface may be added to a dispersion. These additives can be added at various concentrations depending on the purpose and application, and it is preferable to add an additive at such a range of concentration that a fiber can maintain a structure.

Subsequently, the fiber dispersion is placed into a suitable container or molding box in order to fix a fiber in a fiber dispersion in the dispersed state to form a sponge. By arbitrarily changing a shape of a container and a molding box, it is possible to mold the spongelike structure into a desired shape. For example, when the spongelike structure of the present invention is used as a cell scaffold material, the structure is molded into a shape of a tissue or an organ for using tissue regeneration and implant, or various forms such as a column shape, a dish shape, a membrane shape, and a hollow shape for use in cell culture.

Thereafter, the fiber dispersion placed in a container or a molding box is dried to remove a dispersion medium. Examples of a drying method include drying with ambient air, drying with hot air, vacuum drying and freezing drying; from a view point of moldability and in order to obtain the spongelike structure having a small apparent density, freezing drying is preferable. As a method by freezing drying, for example, a dispersion is frozen at not higher than a temperature at which a dispersion medium is frozen, with liquid nitrogen, dry ice or a ultralow temperature freezer. Thereby, the fiber dispersion is fixed in the frozen state, that is, a fiber is fixed in a solid of a dispersion medium in the three-dimensional dispersed state. Thereafter, the dispersion medium is sublimed under vacuum; since thereupon, only the dispersion medium is removed while the fiber is fixed in the three-dimensional dispersion state, it becomes possible to obtain a spongelike structure having a small apparent density and a high porosity. Furthermore, according to the aforementioned method of the present invention, by appropriately selecting a container or a molding box into which a fiber dispersion is placed, it is easy to produce a spongelike structure having a desired shape, that is, the present invention has high moldability.

A temperature at which the fiber dispersion is frozen may be any temperature as far as it is a temperature at which a dispersion medium is frozen, and it is also possible to control a macropore structure of a spongelike structure and the dispersed state of a fiber by a freezing temperature. For example, when water is used as a dispersion medium, freezing is possible at not higher than a solidification temperature of a water (e.g. not higher than 0° C.), and when a freezing temperature is reduced, water which is a dispersion medium is instantly frozen; also, there is a tendency that a crystal of an ice formed during freezing becomes smaller, and association of fibers is suppressed. As a result, the spongelike structure obtained by vacuuming and sublimation of an ice thereafter has a small micropore, and becomes a fine structure. To the contrary, when a freezing temperature approaches 0° C., freezing slowly progresses; also there is a tendency that a crystal of an ice formed during freezing becomes greater, and further, fibers are associated in this process. As a result, the spongelike structure obtained by vacuuming and sublimation of an ice thereafter easily becomes a structure having a macropore in which micropores are communicated. Formation of a crystal of an ice and association of fibers are greatly related not only to a freezing temperature but also to a temperature lowering rate, a pH of a solvent and an additive upon freezing. That is, by controlling a freezing temperature, a time and the state of a solvent, it becomes possible to control a size of a macropore and continuity of micropores of the spongelike structure.

For example, when the spongelike structure of the present invention is used as a cell scaffold material for cultivating a cell as described above, it is ideal that a number mean size of a macropore in the spongelike structure is not greater than 500 μm. For achieving this, when a spongelike structure is formed by freezing drying using water as a dispersion medium, it is preferable to freeze a dispersion at a temperature of not higher than −5° C. In addition, from a relationship between a time until freezing and the crystallization state of an ice, a freezing temperature is more preferably not higher than −20° C. In addition, in order that a cell is retained in the interior of a substrate for cell culture and a culture medium is retained and passed therethrough, a diameter thereof is preferably not smaller than 10 μm, and from that point, a freezing temperature is preferably not lower than −150° C., more preferably not higher than −80° C. Freezing treatment is preferably performed until a dispersion medium is completely frozen, and from that point, a freezing time is preferably not shorter than 2 hours, more preferably not shorter than 6 hours.

In addition, a process of sublimation of a dispersion medium is also greatly related with controlling of a size of a macropore and association of fibers, and controlling of a vacuum degree and a temperature upon sublimation is also important in formation of a spongelike structure. Since a solvent can be rapidly removed by increasing a vacuum degree upon sublimation, association of fibers can be prevented. In addition, a solvent can be prevented from being dissolved by lowering a temperature of sublimation, and it becomes possible to prevent association of fibers also by this.

In addition, when a macropore is provided in a spongelike structure, there is following methods as a procedure of controlling a pore diameter thereof. That is, this is a method of adding a substance consisting of an inorganic salt or the like which has the same size and shape as those of a desired macropore and is not dissolved in a dispersion medium (hereinafter, referred to as porogen in some cases) to a fiber dispersion, removing the dispersion medium by the aforementioned method, and, thereafter, dissolving and removing a porogen by dissolution with a solvent or heat treatment. By such the method, it is also possible to form a macropore having a desired size and shape.

By the aforementioned method, the spongelike structure of the present invention is obtained, and it is possible to subject a fiber being used in the present invention to various treatments depending on the use purpose of the resulting spongelike structure. Examples of the treatment include heat treatment, cooling treatment, freezing treatment, hydrolysis treatment with an acid or an alkali, solvent treatment, hot water treatment, glow discharge treatment, plasma discharge treatment, corona discharge treatment, gamma treatment, EB treatment, laser treatment, UV treatment, IR treatment, ozone treatment, pressure treatment, vacuum treatment, pressurized steam treatment, gas treatment, steam treatment, flame treatment, coating treatment, graft polymerization treatment, drawing treatment, vacuum treatment, crosslinking treatment, chemical modification and ion implementation treatment, being not limiting.

Particularly, when the spongelike structure is used as a cell scaffold material, a surface of the spongelike structure is not a natural substrate for manifestation of the cell function such as adhesion, adherability, growth, proliferation, differentiation inducement and activation of a cell for the purpose of cultivating, in some cases. Then, in order to obtain a surface nature suitable as a cell scaffold material which is a scaffold for cell culture or a scaffold for tissue regeneration, it is preferable to perform various treatments. For example, surface treatment such as coating and graft polymerization is important for variously changing a nature of a fiber surface, and it is also possible to cover a fiber surface with a biocompatible polymer, a biodegradable polymer or a hydrophilic polymer.

Examples of a substance used in such the treatment are not limited to, but include a cationic polymer such as polyvinylpyrrolidone (PVP), polyethyleneimine, polylysine and polyallylamine, an ionic polymer such as an anionic polymer such as polyacrylic acid and polymethacrylic acid, a hydrophilic polymer such as polyvinyl alcohol, polyethylene glycol, polypropylene glycol, cellulose, agarose and silicone, a hydrophobic polymer such as polystyrene, polyethylene terephthalate, polybutylene terephthalate and the like. Alternatively, a surface of a nano-fiber may be coated with a ceramic-based inorganic substance such as hydroxyapatite and tripotassium β phosphate, or a metal-based inorganic substance such as tantalum, titanium, platinum, gold, copper and stainless.

As a substance for performing the coating or graft treatment, a substance having biocompatibility is preferably used. Particularly, bone marrow which is mimicked in a cell scaffold material is constructed of not only a protein such as collagen, but also hydroxylapatite as an extracellular matrix component. For this reason, in that bone marrow is mimicked, it can be said that coating of a fiber with hydroxylapatite is a preferable treatment.

Alternatively, by hydrolysis-treating a fiber surface partially, adsorption property of a serum protein and a protein useful in cell culture onto a surface can be improved. Thereby, manifestation of the cell function such as cell adhesion and adherability can be promoted, or a cell culture density can be also improved.

In the spongelike structure of the present invention, fibers can be also partially fused and adhered by softening, melting, dissolving or re-solidifying a fiber surface in the state where fibers constituting the spongelike structure are dispersed. Representative examples of such the treatment include heat treatment and EB treatment, and, inter alia, pressurized steam treatment is most preferably used. In this case, it is preferable to perform treatment under the temperature condition of not lower than a glass transition temperature of a synthetic polymer used as a raw material of the fiber and not higher than a melting temperature of the polymer. Also, as a treatment method of adhering fibers, adhesion with a coating treated material and fusion by solvent treatment are included as a preferable aspect in addition to the aforementioned treatments. However, adhesion with a coating treated material can adhere fibers by covering a fiber with other polymers to improve durability, but there is a possibility that physical property of a fiber itself is remarkably changed. In addition, there is a high possibility that fusion by solvent treatment changes the dispersed state structure of fibers in the spongelike structure. For this reason, particularly, heat treatment is more preferably used in that the dispersed state of a fiber in the spongelike structure is not changed.

These treatments may be performed either in the state before or the state after production of the spongelike structure, or at any time point, but from a view point of workability, it is particularly preferable to partially adhere fibers by pressurized steam treatment after removal of a dispersion medium.

By partial adhesion of fibers, it becomes possible to improve durability to an external physical force such as water resistance and pressure resistance while the dispersed state of a fiber in the spongelike structure is retained.

In addition, in order to optimally use the spongelike structure of the present invention as a cell scaffold material, it is preferable to adhere and/or immobilize a functional substance onto a surface of a fiber constituting the spongelike structure. As used herein, adsorption refers to the state where a substance and a substance are physically bound by the hydrophobic interaction which is caused due to low affinity for water. In addition, immobilization refers to the state where a substance and a substance are bound by a chemical bond, a representative of which is a covalent bond.

As a method of adhering a functional substance onto a fiber surface, it is enough that a functional substance is contacted with a fiber surface. For example, it is enough that a fiber is immersed in a solution in which a functional substance is dissolved with a solvent. Thereupon, since a fiber, particularly a nano-fiber used in the present invention has a great specific surface area, adsorption is caused; by heat treatment or long term treatment, adsorption is promoted.

Examples of a method of immobilizing a functional substance on a fiber surface include a method of reacting a functional group on the fiber surface and a functional group of the functional substance to perform covalent binding or ion binding. Examples of a functional group of such the functional substance include a carboxyl group, an amino group, a mercapto group, a pyridyl disulfide group, an isocyanate group, a hydroxyl group, a phenylazido group, a diazocardene group, a hydrazine group, a N-hydroxysuccinimide group, an imidoester group, a nitroaryl halide group, an imidazolylcarbamic acid group, maleimide group, a thiophthalimide group and an activated halogen. In order to introduce such the functional group into a fiber surface, a polymer or a molecule having such the functional group may be used as a raw material at fiber production, or may be coated on a fiber surface to adsorb thereon. Alternatively, an active group may be introduced into a fiber surface using a commercially available crosslinking agent having an active group which reacts with two kinds of different functional groups. Alternatively, a functional group having specific binding property such as a biotin group, an avidin group, streptavidin and polyhistidine may be introduced into a fiber surface.

These functional substances may be adsorbed and/or immobilized onto a fiber before formation of the spongelike structure, or may be adsorbed and/or immobilized onto a constitutional fiber of the spongelike structure after formation of the structure. Specifically, when the functional substance is adsorbed and/or immobilized on a fiber before formation of the spongelike structure, for example, a functional substance may be added to a fiber dispersion before formation of the spongelike structure. Alternatively, the functional substance may be contained in a polymer alloy fiber which is a precursor to a fiber. When the functional substance is adsorbed and/or immobilized onto a constitutional fiber of the spongelike structure after formation of the structure, this may be performed by post-processing such as coating and the like.

The functional group itself may be directly adsorbed and/or immobilized onto a fiber surface, or after a precursor substance of the functional substance may be adsorbed and/or immobilized onto a fiber surface, the precursor substance may be converted into a desired functional substance. Specifically, there is a method of impregnating the spongelike structure consisting of a fiber with an organic substance, and thereafter, chemically changing it by external treatment. For example, there are a method of impregnating the spongelike structure consisting of a nano-fiber with an easy soluble substance by treatment in a bath, and converting the substance into a low soluble substance by an oxidation and deduction method, ligand substitution, a counter ion exchange reaction, an enzyme reaction, a photochemical reaction or a hydrolysis reaction, and a method of converting into a structure of an activated body. Alternatively, when a precursor of the functional substance is adsorbed in a process of fiber spinning, a method of converting into a molecular structure having high heat resistance in a spinning process, and returning into a molecular structure which manifests the function by post-processing may be adopted.

When the functional substance is adsorbed onto a fiber surface, it is preferable to use a nano-fiber. By doing so, not only a specific surface area is dramatically increased, but also a few nm to a few hundreds nm spaces are indefinitely formed between fibers in the spongelike structure. As a result, excellent adsorption and absorption properties peculiar to a nano-fiber which have not been seen in the previous fiber such as a micro-fiber are exhibited, and it becomes possible to adsorb and retain the functional substance onto a nano-fiber at a high density. Moreover, it becomes possible to manifest the carrying function by the functional substance maximally, as the spongelike structure.

The functional substance refers to a general substance which can improve the function as a cell scaffold material. For example, a moisture absorbent, a humectant, a water repellant, a heat-retaining agent, a surface modifier and a smoothing agent can be also used as a functional substance. More specifically, in a sense that physical property or biological property of a surface of a nano-fiber is improved, a polymer, a low-molecular substance and a drug such as amino acid, protein, vitamins, steroids, sugars, polyamine and a photo catalyst can be used.

In order to obtain an optimal form for using the spongelike structure of the present invention as a cell scaffold material in cell therapy or regenerative therapy, it is preferable to adsorb and/or immobilize a protein which directly influences on manifestation of the cell function such as cell adhesion, cell proliferation or differentiation and activation as a functional group, on a fiber surface. Examples of such protein include cytokine which is an important functional protein for cell adhesion, cell proliferation and cell function. Cytokine refers to a protein exhibiting the physiological activity via a specific receptor on a cell surface at an extremely small amount, and collectively refers to a protein which is responsible for regulation of immunity, regulation of an inflammation reaction, disorder or death of a virus-infected cell or a tumor cell, and proliferation and differentiation of a cell.

Cytokine includes interleukin, growth factor, chemokine, tumor necrosis factor and interferon. Specifically, examples include insulin, IGF (insulin like growth factor)-I, IGF-II, EGF (epithelial growth factor), TGF (transforming growth factor)-α, TGF-β1, TGF-β2, FGF (fibroblast growth factor)-1, FGF-2, FGF-3, FGF-4, FGF-5, FGF-6, FGF-7, FGF-8, FGF-9, FGF-10, FGF-11, FGF-12, FGF-13, FGF-14, FGF-15, FGF-16, FGF-17, FGF-18, FGF-19, VEGF (vascular endothelial growth factor)-A, VEGF-B, VEGF-C, VEGF-D, NGF (nerve growth factor), IL (interleukin)-1α, IL-1β, IL-2, IL-3, IL-4, IL-5, IL-6, IL-7, IL-8, IL-9, IL-10, IL-11, IL-12, IL-13, IL-14, IL-15, IL-16, IL-17, IL-18, GM-CSF (granulocyte-macrophage colony stimulating factor), G-CSF (granulocyte colony stimulating factor), M-CSF (macrophage colony stimulating factor), SCF (stem cell factor), FL (flt-3 ligand), angiopoitin, EPO (erythropoietin), TPO (thrombopoietin), OSM (oncostatin M), LIF (leukemia inhibitory factor), activin, inhibin, BMP (bone morphogenetic protein), PDGF (platelet derived growth factor), HGF (hepatocyte growth factor), TNF (tumor necrosis factor)-α, TNF-β, Fas-L (Fas ligand), CD40 ligand, MIP (macrophage-inflammatory protein), MCP (monocyte chemoattractant protein), IFN (interferon)α, IFNβ, IFNγ, GDNF (glial cell line-derived neurotrophic factor), and angiotensin, being not limiting.

In addition, examples of a protein which influences on a cell other than cytokine include Notch ligand (Delta 1-3, jugged/serrate 1,2), a stimulation antibody such as an anti-CD3 antibody and an anti-CD28 antibody, T cell receptor (TCR), Wnt secreted protein, and Tie receptor, and these may be also used.

In addition, as a protein effective in cell culture and tissue regeneration, there is a protein involved in adhesion of a cell called extracellular matrix or adhesion factor, and adsorption and/or immobilization of such the protein onto a nano-fiber is also effective from a view point of cell culture and tissue regeneration.

The extracellular matrix refers to a complicated complex of biological polymer compounds which are synthesized by a cell, and secreted and accumulated extracellularly. That is, a structural support of a tissue which is sedimented around a cell corresponds to this, and adjusts cell adhesion, orientation of a cell skeleton, a shape of a cell, cell migration, cell proliferation, intracellular metabolism and cell differentiation. Examples of the extracellular matrix include fibronectin laminin, collagen, glycosaminoglycon (heparin sulfate, hyaluronic acid etc.), heparin, chitin, and chitosan.

The adhesion factor refers to a factor which is present on a cell surface and is involved in adhesion between cell-cell and between cell-extracellular matrix. Examples of the factor involved in adhesion between cell-cell include cadherin family, Ig super family, selectin family and sialomucin family. In addition, examples of the factor involved in adhesion between cell-extracellular matrix include integrin family.

Specifically, examples include a full or partial protein of an artificially synthesized peptide or an extracellular matrix, and include "Pronectin F" (registered trademark), "Pronectin L" (registered trademark) manufactured by Sanyo Chemical Industries, Ltd., and "Retronectin" (registered trademark) manufactured by TAKARA SHUZO Co., Ltd. as genetically modified proteins.

The aforementioned proteins can be used alone or in combination of two or more kinds.

As a cell scaffold material, it is preferable in some cases that the functional substance once adsorbed onto a fiber surface is gradually released, because it first becomes possible to impart the function to a cell by release of the functional substance, in some cases.

When the cell scaffold material is constructed of a nano-fiber, a functional substance adsorbed and retained onto a fiber surface at a high density, or a functional substance absorbed and retained between fibers exhibits sustained release that it is released from a fiber surface or between fibers over a long period of time. Therefore, a functional substance such as a protein adsorbed onto a nano-fiber surface or absorbed between nano-fibers exhibits such a nature that it is released into a culture medium over a long period of time after adsorption or adsorption. An amount and a term of release depend on a nature of a nano-fiber surface, an amount of an adsorbed or absorbed functional substance, a nature of a functional substance itself, and the environment such as a pH, a temperature and a salt concentration.

For example, regarding a functional substance adsorbed by the hydrophobic interaction, as a nano-fiber surface is closer to hydrophilic, the function is more easily released. As a trial of enhancing such the sustained release, a method of using a hydrophilic polymer as a material for a nano-fiber, or hydrolyzing a nano-fiber surface with, for example, hydrochloric acid or sodium hydroxide in order to render a nano-fiber surface hydrophilic, a method of coating with a hydrophilic polymer and the like may be adopted. In this case, it is necessary to consider balance between adsorbability and sustained release.

Alternatively, upon sustained release of a functional substance adsorbed onto a nano-fiber surface into a solution, by making the easily sustained release environment, for example, by adding a high adsorbable substance such as a high-molecular protein to a solution such as a culture medium, an amount of release of a functional substance from a nano-fiber can be increased. Examples of the high adsorbable substance to be added to a solution such as a cell culture medium for such the purpose include albumin, serum protein, milk protein, skimmed milk and lipid, and by adjusting an addition amount of those high adsorbable substances, it becomes possible to adjust a release amount and a sustained release term of a protein. In addition, when a degradable polymer such as polylactic acid is utilized as a material for a nano-fiber being used, it is possible to gradually release an adsorbed or absorbed protein with degradation of a polymer itself. Further, after a degradable substance such as gelatin is adsorbed onto a nano-fiber surface and retained thereon, a functional substance is adsorbed or absorbed thereon; thereby, it is also possible to gradually release the substance.

A cell scaffold material comprising the spongelike structure of the present invention is suitably used for cell culture or tissue regeneration. "For cell culture" refers to an application of causing manifestation of the function such as proliferation, adhesion, ambulation and differentiation on a scaffold material. In addition, "for tissue regeneration" refers to an application of making a tissue in vivo or in vitro in which an aggregate of cells having similar work form has a function, on a scaffold material, and it is also possible to form an organ by gathering various tissues on a cell scaffold material.

Specifically, a cell scaffold material comprising the spongelike structure of the present invention can be used to cultivate one or more kinds of cells such as living body-derived cells such as a hematopoietic stem cell, a neural stem cell, a mesenchymal stem cell, a mesodermal stem cell, an ES cell (embryonic stem cell), a pluripotent stem cell, a CD34 positive cell, an immune cell, a hematopoietic cell, a neural cell, a vascular endothelial cell, a fibroblast cell an epithelial cell, a hepatocyte, a beta cell of pancreas, a myoblast, an osteoblast, a chondrocyte, a myoblast cell, a bone marrow cell, an amniotic cell and an umbilical cord blood cell, established cells such as a NIH3T3 cell, a 3T3-L1 cell, a 3T3-E1 cell, a Hela cell, a PC-12 cell, a P19 cell, a CHO (Chinese hamster ovary) cell, a COS cell, a HEK cell, a Hep-G2 cell, a CaCo2 cell, a L929 cell, a C2C12 cell, a Daudi cell, a Jurkat cell, KG-la cell, a CTLL-2 cell, a NS-1 cell, a MOLT-4 cell, a HUT78 cell and a MT-4 cell, various hybridoma cell strains which are an antibody-producing cell, and cells obtained by modifying these cells by genetic engineering.

That is, a cell scaffold material comprising the spongelike structure of the present invention, as its application, can be used as a part or all of bag, flask, disc, well, petri dish, dish, plate, multi-well well, multi-well plate, slide, film, column, tank, bottle, hollow thread, non-woven fabric, and molded articles of sphere, particle and flake which are used in cell culture, as a part or all of molded articles for a cell scaffold material used in formation of tissues for tissue regeneration and transplantation of nerve, heart, blood vessel, cartilage, skin, cornea, kidney, liver, hair, cardiac muscle, muscle and tendon, as a part or all of in vivo embedding medical molded articles such as an aneurysm coil, an embolus substance, an artificial nerve, an artificial mucosa, an artificial esophagus, an artificial airway, an artificial blood vessel, an artificial valve, an artificial chest wall, an artificial pericardium, an artificial cardiac muscle, an artificial diaphragm, an artificial peritoneum, an artificial ligamentum, an artificial tendon, an artificial cornea, an artificial skin, an artificial joint, an artificial cartilage, a dental material and an intraocular lens, as a part or all of molded articles used in a medical act such as a surgical suture, a surgical prosthetic material, a surgical reinforcing material, a wound protecting agent, an adhesion preventing agent, a fracture jointing agent, a catheter, a syringe, a fluid infusion/blood bag, a blood filter and an extracorporeal circulation material, or as a part or all of materials such as a contact lens, and an intraocular lens, and molded articles. In addition, these molded articles can be used not only in medical application, but also in experimental application and analytic application.

When a cell scaffold material comprising the spongelike structure of the present invention is formed into a desired shape, and cell cultivating or tissue cultivating is performed in vitro using this as a scaffold for the cultivating, as a cell culture medium, for example, commercially available cell culture media called Minimum Essential Medium (MEM), Basal Medium Eagle (BME), Media 199, Dulbecco's Modified Eagle Medium (D-MEM), α-Minimum Essential Medium (α-MEM), F-10 Nutrient Mixture (Ham's F-10, Ham F 10 medium), F-12 Nutrient Mixture (Ham's F-12, Ham F 12 medium), RPMI1640, L-15, Iscove's Modified Dulbecco's Medium (IMDM), ES medium, MCDB 131 Medium, CMRL 1066 Media, DM-160 Medium, Fisher Medium, StemSpan Medium, StemPro Medium, Hybridoma Serum Free Medium, various buffers such as phosphate buffer, acetate buffer, Tris-hydrochloric acid buffer, carbonate buffer, glycine-hydrochloric acid buffer, citrate buffer, HEPES buffer, MOPS buffer and Hanks buffer, and a mixture thereof can be used; a cell culture medium optimal for a cell to be cultivated may be used, being not limiting.

In addition, to these culture media may be added additives such as serum such as bovine serum, bovine fetal serum, equine serum, plasma components, cytokine such as interleukin, interferon and insulin, amino acid such as alanine, asparagine, glycine, prolin, arginine, histidine and lysine, transferrin, selenium, mercaptoethanol, and ascorbic acid.

When cell culture is performed using the cell scaffold material of the present invention, the stationary state or the flowing state may be used. As the flowing state, culture may be performed by suspension culture, circulation culture, rotation culture or stirring culture. In addition, upon cell culture, a cell can be cultivated in a 5% $CO_2$ incubator, a cell can be cultivated in a gas permeable bag, a cell can be cultivated by incorporating a cell scaffold material comprising the spongelike structure of the present invention into a column, or a cell can be cultivated utilizing a perfusion culture system in which a reservoir containing a cell suspension, an oxygen loading device utilizing a commercially available artificial lung, or a dialysis column for exchanging a medium is incorporated. In addition, when a cell itself or a solution in which a cell is suspended is added to the cell scaffold material of the present invention, it is also possible to add a cell to the interior of the spongelike structure utilizing a syringe-like equipment having a thin needle at a tip, in order to uniformly seed cells on a three-dimensional spongelike structure. After the spongelike structure is exposed to the low pressure state, cells are added, and they can be uniformly seeded. In addition, after cells are seeded, the spongelike structure can be shaken to make cells uniformly present in the structure.

The aforementioned culture medium and additive for cell culture may be impregnated into a cell scaffold material comprising the spongelike structure of the present invention in advance, and a cell may be added thereto, thereby, the cell can be cultivated. By adopting such the method, operability of a cultivated cell is improved.

The cell scaffold material may be the spongelike structure of the present invention alone, or construction of laminating the spongelike structure on other substrate may be adopted. The substrate may be a material which becomes a foundation, a base or a basis, and plays a role in supporting the spongelike structure and stabilizing a shape. A shape of the substrate may be a sheet or a steric structure, and the shape is preferably a shape when actually used as an equipment for cell culture or a medical equipment.

The cell scaffold material comprising the spongelike structure of the present invention can be also used in producing a transplantation cell which is used in cell therapy, a representative of which is stem cell transplantation, and regenerative therapy. For example, in recent years, for a serious blood patient such as leukemia, hematopoietic stem cell transplantation using, particularly, umbilical blood in place of bone marrow as a supply source is performed. Transplantation using umbilical blood is used for treating acute lymphocytic leukemia (ALL), acute myelocycic leukemia (AML), aplastic anemia, congenital immunodeficiency and congenital dysbolism; since graft-versus-host disease (GVHD) after transplantation is slighter as compared with bone marrow transplantation and peripheral blood stem cell transplantation, and the proliferation ability is vigorous, transplantation becomes possible even at the cell number which is around 1/10 the cell number used at bone marrow transplantation. However, since an absolute total cell number of a stem cell contained in umbilical blood is small, and it is difficult to maintain the number of cells necessary for take of a hematopoietic stem cell in an adult, transplantation has been performed mainly on an infant in the previous transplantation. For this reason, for example, by proliferating a hematopoietic stem cell and a precursor cell in umbilical blood while maintained in the undifferentiated state, using a cell scaffold material of the present invention mimicking the in vivo environment, a stem cell and a precursor cell which can be transplanted into an adult can be maintained, and extension of application of stem cell transplantation to an adult, avoidance of insufficient take, promotion of hematopoietic restoration, alleviation of blood infusion amount, transplantation to a plurality of patients, plural times transplantation to one patient, shortening of an in hospital term of a patient, and safer transplantation can be achieve. In addition, the cell scaffold material of the present invention mimicking the in vivo environment can be also used for cultivating a transplantation cell such as a helper T cell, a killer T cell and a dendritic cell which are used in cancer immunological therapy. Like this, in order to cultivate a stem cell, a precursor cell or an immune cell, it is preferable that cytokine which is one kind of proteins inducing the function of proliferating a cell or dividing a cell is absorbed onto the cell scaffold material comprising the spongelike structure of the present invention, thereby, cytokine is gradually released.

When the spongelike structure of the present invention is used as a cell scaffold material for cell culture, a cell effective for various diseases and conditions can be also cultivated to produce a cell preparation. The cell preparation refers to a drug or a medical equipment obtained by processing a tissue or a cell, and a process for producing a cell preparation includes all steps for processing a cell into a form effective for a disease and a condition as a cell preparation, such as separation of a cell, proliferation of a cell, stimulation of a cell, inducement of cell differentiation, and cell apoptic inducement.

In order to produce a cell preparation, first, a tissue or a body fluid which is to be a supply source for cell groups is collected. A supply source of these cell groups is preferably human-derived, being not limiting. Examples of such the supply source of a cell group include peripheral blood, umbilical blood, bone marrow liquid, amniotic membrane tissue, placental tissue, reproduction nidus, G-CSF-mobilized peripheral tissue and fetal tissue, being not limiting. Particularly, when a body liquid is used as a supply source, it is general to obtain a uniform cell group from which an extra component for cell culture has been removed, in advance, by a centrifugation method, a unit gravity settlement method or a centrifugation selection method before cultivating. Further, it is preferable to obtain a cell group having a high purity of a cell to be transplanted, using a method of separating cells such as flow cytometry, a magnetic beads method and an affinity column method before cell culture. After such the various processings, by performing cell culture or tissue regeneration using the cell scaffold material comprising the spongelike structure of the present invention, a necessary cell as a cell preparation can be obtained at a high purity.

Upon production of a cell preparation, it is preferable to re-perform cell separation using the cell scaffold material after a cell is cultivated. By doing so, an objective useful cell can be obtained at a large scale and a high purity, and a cell preparation excellent in the effect can be produced.

The spongelike structure of the present invention can be also used as an implant material which is inserted into a living body. By promoting the activity of a variety of functional cells on the spongelike structure having a shape corresponding to a shape of a tissue or an organ such as bone, nerve and muscle, cells can be three-dimensionally distributed, and regeneration and reconstruction of a tissue and an organ having a particular shape can be promoted while the function of a cell is controlled.

Since the spongelike structure of the present invention has a small apparent density and a high porosity as described above, it is useful in industrial material application and household wares application such as a light reflective plate used for a liquid crystal, a buffering material and a water retention material in addition to the aforementioned heat insulator, acoustic material and cell scaffold material. Examples include a cushioning material for vehicle interior decoration, a ceiling material, a construction material, a wiping, a stain cleaning sheet, a health product, and a sensor member for IT member.

In addition, since the spongelike structure has a micropore of a network structure, it is suitable in filter application, and can be utilized from household wares application to industrial application such as an air filter and a liquid filter, and medical application such as a blood filter. Examples include the fields in which an air filter for a clean room, an automobile, ventilation of a factory and an incineration facility, and a house, a liquid filter for a chemical process, a food, a drug and medicine, or a HEPA or ULPA filter is applied.

Further, the spongelike structure is suitable not only as a filter, but also as a sponge for wiping, polishing and abrasion utilizing flexibility, surface smoothness, and wiping property of the spongelike structure, and is of course suitable in a beauty cosmetic equipment, a cleansing sheet, and a skin care sheet, and a medical extracorporeal circulation column, a bandage and an adhesive skin patch.

Subsequently, a powder consisting of an ultramicrofiber of the present invention will be explained together with a desirable embodiment.

In the present invention, the powder refers to a granular structure in the dry state like a general inorganic particle. A shape is from a shape close to a true sphere to a flat or rod-like form, and the shape is not particularly limited. The powder of the present invention is a granular structure obtained by aggregating or entangling the same fibers (number mean diameter is different) as those explained for spongelike structure while not oriented. Herein, "aggregated while not oriented" refers to the state where single fibers in a powder are present in the separate state, and an intersection between single fibers is bonded by an intermolecular force or a hydrogen bond force. In addition, the "entangled" refers to the state where an intersection between single fibers is bonded by entanglement between single fibers. As one example of the powder in the present invention, a scanning electron microscope (SEM) photograph of the powder obtained in Example 34 described later is shown in FIG. 5 and FIG. 6.

In a fiber constituting the powder of the present invention, it is important that a number mean diameter is 1 to 500 nm. By adopting a number mean diameter of the fiber in such the range, since fibers are easily dispersed in a dispersion medium from a view point of a production step, fibers are easily present uniformly without partial unevenness in the powder, and there is an advantage that a powder having a small apparent density and a high porosity is easily obtained. A number mean diameter of the fiber is preferably 1 to 200 nm, further preferably 1 to 100 nm. In addition, a number mean diameter of the fiber can be obtained by observing a surface of a powder with SEM and calculating a diameter of a single fiber as explained for the spongelike structure.

In addition, the powder of the present invention has its number mean diameter of 1 to 1000 μm. By adopting such the particle diameter range, the powder can be blended at better dispersity when blended into a resin, a paint and a cosmetic; further, when they are coated, powders are not aggregated to become an undissolved mass, and it becomes possible to coat them uniformly. A number mean diameter is more preferably 1 to 200 μm, further preferably 1 to 100 μm.

In the present invention, a number mean diameter of the powder can be obtained as follows: that is, a particle diameter of a powder is calculated a diameter of a sphere equivalent to the powder from the aforementioned photograph of the powder by SEM observation, using a commercially available image processing software, and a simple average thereof was obtained. Thereupon, a particle diameter of 150 powders randomly extracted in the same field is analyzed, and a number mean is calculated.

A kind of a fiber constituting the powder of the present invention is the same that of the spongelike structure, and inter alia, a thermoplastic polymer is preferable. A polymer may contain an additive such as particles, a flame-retardant, an antistatic agent. Other component can be copolymerized in such a range that a nature of the polymer is not deteriorated.

Then, a process for producing the powder of the present invention will be explained.

A process for producing the powder of the present invention is fundamentally the same as the process for producing the spongelike structure, in which fibers having the aforementioned number mean diameter in a particular range are dispersed in a dispersion medium to prepare a fiber dispersion, and the fiber dispersion is dried to remove a dispersion medium. Thereupon, in order that the finally obtained fiber dispersion has a powder shape of the aforementioned particle diameter, it is necessary that a fiber having a number mean diameter of 1 to 500 nm is used as a fiber to be dispersed in a dispersion medium, and the fiber dispersion is granulated, and dried to remove the dispersion medium.

In addition, a fiber to be dispersed in a dispersion medium is cut into a desired fiber length, and is dispersed in a dispersion medium. Thereupon, for the same reason as that of the spongelike structure, it is preferable that a constitutional ratio of single fibers having a diameter of greater than 500 nm is not more than 3% by weight.

Examples of a drying method of drying a fiber dispersion to remove a dispersion medium include drying with ambient air, drying with hot air, vacuum drying, freezing drying and the like. For example, although the powder of the present invention can be obtained by freezing a fiber dispersion, trimming this into a spherical shape by grinding or various procedures, and further, freezing and drying this, it is preferable to obtain the powder of the present invention by spray drying in order to obtain a powder having a smaller particle diameter. In spray drying, using a spray drying device, a dispersion medium is removed with hot air while a dispersion is sprayed as fine liquid droplets, and a powder is captured. Thereby, a powder in which fibers gather in the approximately spherical state is obtained. As a method of spraying liquid droplets, various methods such as a method of spraying with a nozzle and a method of flying liquid droplets with a rotation disc can be adopted.

A number mean diameter of the powder of the present invention is 1 to 1000 μm; when formulated into a powder by spray drying, a number mean diameter of a powder particle can be controlled at 1 to 1000 μm by adjusting a diameter of liquid droplets, a concentration of a fiber in a fiber dispersion, a diameter of a fiber and the like. That is, since a powder diameter does not become greater than a diameter of liquid droplets, a number mean diameter of a powder can be controlled by mainly adjusting a diameter of liquid droplets and a fiber concentration of a fiber dispersion. A diameter of liquid droplets can be adjusted by a structure of a nozzle and a spraying rate in the case of a method of spraying with a nozzle, and can be adjusted by a falling rate of a dispersion and a rotation rate of a disk in the case of a method of flying liquid droplets with a rotation disc.

Further, for the same reason as that of the spongelike structure, it is preferable that fibers are partially fused and adhered, by softening, melting, dissolving or resolidifying a surface of an aggregated or entangled fiber after removal of a dispersion medium.

In addition, since preparation of a fiber dispersion and drying and removal of a dispersion medium are the same as those explained for the spongelike structure, explanation will be omitted.

Since the powder of the present invention obtained as described above has a small particle diameter, it can be suitably used, for example, upon production of a paint and a cosmetic.

When the powder of the present invention is applied to a paint, the paint is composed of the powder of the present invention and a solvent, and the powder of the present invention is dispersed in a solvent. Various additives such as a viscous agent for adjusting a viscosity and a dispersant for improving dispersity may be further blended into the paint. A kind of the solvent and various additives is not particularly limited, but may be appropriately selected depending on the purpose and the application. Examples of the solvent include the following organic solvent, such as alcohols, esters, glycols, glycerins, ketones, ethers, amines, lower fatty acids such as lactic acid and butyric acid, pyridine, tetrahydrofuran, furfuryl alcohol, acetonitrile, methyl lactate, and ethyl lactate; these can be used alone or in combination of two or more kinds.

On the other hand, when the powder of the present invention is applied to a cosmetic, the cosmetic is composed of the powder of the present invention, various active components and a solvent. A form thereof may be liquid or solid.

As the solvent, there can be exemplified water, an oil, and an organic solvent, and these can be used by appropriately combining them. Examples of the oil include natural oils such as a linseed oil, a corn oil, an olive oil, a sunflower oil, a rapeseed oil, a sesame oil, a soybean oil, a cacao oil, a coconut oil, a palm oil, and a haze wax, paraffin, vaseline, seresin, liquid paraffin, squalane, wax, higher fatty acid, silicone oil, and crosslinked silicone oil; these can be used alone or in combination of two or more kinds. As the organic solvent, the same organic solvent as that described for the powder can be used, and solvents can be used alone or in combination of two or more kinds.

Examples of the active ingredient include various amino acids, proteins and vitamins, specifically, various components which give moisture retaining property and moisture to a skin and retain a skin fresh, such as hyaluronic acid, kojic acid, collagen, ceramide, squalane, lecithin, ascorbic acid which is a main component of vitamin C, and tocopherol which is a main component of vitamin E.

As described above, the powder of the present invention is useful as a filler for a paint and a cosmetic, and the powder of the present invention is also useful as a filler for a resin. In addition, the powder of the present invention is also useful in an adsorbent or a water retaining agent utilizing its surface area, and, further, is suitable in a powdery material in each field of medicine, hygiene and the like.

EXAMPLES

The present invention will be explained in detail below using Examples. In a measurement method in Examples, the following methods were used.

A. Melt Viscosity of Polymer

A melt viscosity of a polymer was measured with Capillograph 1B manufactured by Toyo Seiki Seisaku-sho, Ltd. A time for retaining a polymer from sample charging to measurement initiation was 10 minutes.

B. Melting Point of Polymer

A peak top temperature showing melting of a polymer in $2^{nd}$ run as obtained using DSC-7 manufactured by Perkin Elmer was adopted as a melting point of a polymer. Thereupon, a temperature raising rate was 16° C./min, and a sample amount was 10 mg.

C. Uster Unevenness (U %) of Polymer Alloy Fiber

Using USTER TESTER 4 manufactured by Zleeweger uster, measurement was performed in a normal mode at a yarn supplying rate of 200 m/min.

D. SEM Observation of Spongelike Structure and Powder

A sample was deposited with platinum, and this was observed with a field emission scanning electron microscope. SEM apparatus: UHR-FE-SEM manufactured by Hitachi, Ltd.

E. Observation of transverse section of fiber with TEM

Using a fiber bundle before dispersing, an ultrathin strip was cut out in a transverse section direction thereof, and the transverse section of a fiber was observed with TEM. In addition, metal staining was used, if necessary.

TEM apparatus: Model H-7100FA manufactured by Hitachi, Ltd.

F. Number Mean Diameter of Fiber

A number mean diameter of an island component in a polymer alloy fiber and a number mean diameter of a single fibers (nano-fiber) of a fiber bundle are obtained as follows: That is, the fibers were observed with TEM in the above item E at such magnification that at least 300 island components can be observed in one field in the case of the polymer alloy fiber, and at least 300 single fibers can be observed in one field in the case of a fiber bundle, and a simple average of each diameter of an island and a single fiber was obtained from the observed photograph using an image processing software (WINROOF). Thereupon, 300 diameters in the case of the island component, and 300 diameters in the case of a single fiber, which were randomly extracted in the same field, were analyzed, and used in calculation.

On the other hand, a number mean diameter of a single fiber constituting the spongelike structure or the powder is obtained as follows: That is, the fibers was observed with SEM in the item D at such magnification that at least 150 or more single fibers can be observed in one field, and letting a fiber width in a direction perpendicular to a fiber longitudinal direction to be a diameter, a simple average thereof was obtained from the observed photograph using an image processing program (WINROOF). Thereupon, 150 fiber diameters which were randomly extracted in the same field were analyzed, and used in calculation.

G. Constitutional Ratio of Single Fibers in Fiber Bundle

Utilizing analysis of a diameter of a single fiber in the fiber bundle, and letting a diameter of each single finer in a fiber bundle to be $d_i$, a square sum $(d_1^2+d_2^2+ \ldots +d_n^2)=\Sigma d_i^2$ ($i=1\sim n$) is calculated. In addition, letting a diameter of each single fiber having a diameter of greater than 500 nm in a fiber bundle to be $D_i$, a square sum $(D_1^2+D_2^2+ \ldots +D_m^2)= \Sigma D_i^2$ ($i=1\sim m$) is calculated. By calculating a ratio of $\Sigma D_i^2$ relative to $\Sigma d_i^2$, an area ratio of bulky fibers relative to a whole fiber, that is, a constitutional ratio was obtained.

H. Mechanical Property of Fiber (Before Dispersing)

A load-elongation curve was obtained under the condition shown in JIS L 1013 at room temperature (25° C.), an initial sample length=200 mm and a tensile rate=200 mm/min. Then, a load value at breakage was divided by an initial fineness; this was adopted as a strength. An elongation at breakage was divided by an initial sample length, and this was adopted as elongation.

I. Apparent Density of Spongelike Structure

A spongelike structure is cut into a shape such as a cube and a cuboid, a size of each side is measured using a ruler or a slide caliper, a volume of the spongelike structure is obtained, and this is designated as V (cm³). In addition, a weight of the excised structure is measured, and this is designated as W (g). By dividing W by V, an apparent density $\rho_a$ is obtained.

J. Porosity of Spongelike Structure

Using a volume V (cm³) and W (g) used when the apparent density was obtained, and, further, using a specific gravity $S_u$ (g/cm³) of a fiber forming the spongelike structure, a porosity is obtained by the following equation.

$$F_V(\%)=(W_f/S_f)/V \times 100 \quad (1)$$

Thereupon, when a component other than a fiber, for example, an additive is contained, a porosity is obtained, for example, using the following equation (2) considering also a density and a weight of the additive. Further, when a plurality of additives are contained, a porosity can be obtained by the similar idea.

$$F_V(\%)=(W_f/S_f)+(W_t/S_t))/V \times 100 \quad (2)$$

Wherein, $W_f$: weight of fiber, $S_f$: specific gravity of fiber, $W_t$: weight of additive, $S_t$: specific gravity of additive.

K. Number Mean Size of Micropore in Spongelike Structure

First, a frame of a regular square having one side of 50 mm is drawn at an arbitrary position on the SEM photograph taken in the item D. Further, a fiber image in the frame is inputted into an image processing software (WINROOF). In order to digitalized an image, arbitrary 8 or more luminance distribution measuring lines were superposed on the inputted image at an equal interval, and luminance distribution of each fiber thereon is measured. Ten fibers from a higher surface luminance are selected, and a luminance is averaged to obtain an average high luminance Lh. Letting a luminance which is 50% of the average high luminance Lh to be a threshold Lu, fibers having a luminance of not higher than Lu are deleted by image processing (Threshold function) (this processing results in selection of pores around a surface part). An area Ai (nm²) surrounded by selected fibers is measured by image processing at all numbers (manual working or computer automatic manner is possible). Ai is divided by a pore number n, and a diameter of a circle equivalent to the pore is obtained from that value, thereby, a number mean size is obtained.

L. Number Average Size of Macropore in Spongelike Structure

In the SEM photograph taken in the item D, among pores surrounded with a wall structure formed by aggregation of fibers, 50 pores having a diameter of a circle equivalent to the pore of not smaller than 1 μm are arbitrarily selected, and a sum of the 50 diameters of a circle equivalent to the pore is subjected to simple averaging to obtain a number average size.

M. Heat Conductivity of Spongelike Structure

A heat conductivity is measured according to "Method of measuring heat resistance and heat conductivity of heat insulating material-Part 2: Heat flow meter method" described in JAS-A1412-2 (1999). A 20 cm-square sample is held with protective heat plates, a heat conductivity at least two or more points is measured between room temperature to 80° C.; a first order straight line between a measurement temperature and the resulting value is obtained, and a heat conductivity value $\lambda_0$ when extrapolated at a temperature of 0° C. is obtained.

N. Sound Absorption Rate of Spongelike Structure

A sound absorption rate is measured according to "Perpendicular incident sound absorption rate measuring method" described in JIS-A 1405 (1999). A measurement range is a frequency of 100 to 2000 Hz (A acoustic tube) and 800 to 5000 Hz (B acoustic tube). A sample size was 91.6 mmφ in the case of the A acoustic tube, and 40.0 mmφ in the case of the B acoustic tube.

O. Number Mean Particle Diameter of Powder

Powders were observed with the SEM of the item D at such magnification that at least 150 powders can be observed in one field, a diameter of a sphere equivalent to the powder particle was calculated from the observed photograph using image processing software (WINROOF) as the diameter of the powder, and a simple average thereof was obtained. Thereupon, a particle diameter of 150 powders which were randomly extracted in the same field was analyzed, and used in calculation.

Production Example 1 of Dispersion

N6 (20 weight %) having a melt viscosity of 57 Pa·s (240° C., shearing rate 2432 sec⁻¹) and a melting point of 220° C., and poly-L lactic acid (optical purity 99.5% or higher) (80 weight %) having a weight average molecular weight of 120 thousands, a melt viscosity of 30 Pa·s (240° C., shearing rate 2432 sec⁻¹) and a melting point of 170° C. were melted and kneaded with a double-screw extruder at 220° C. to obtain a polymer alloy chip. A melt viscosity of N6 at 262° C. and a shearing rate of 121.6 sec⁻¹ was 53 Pa·s. In addition, a melt viscosity of this poly-L lactic acid at 215° C. and a shearing rate of 1216 sec⁻¹ was 86 Pa·s. In addition, the kneading condition thereupon was as follows.

Polymer supply: N6 and poly-L lactic acid were separately weighed, and supplied to a kneader separately.
Screw type: Same directional complete fitting type W-start thread
Screw: diameter 37 mm, effective length 1670 mm, L/D: 45.1
A kneading part length is positioned on a discharge side from ⅓ a screw effective length
Temperature: 220° C.
Vent: 2 places This polymer alloy chip was melted in a melting part at 230° C., and was introduced into a spin block at a spinning temperature of 230° C. Then, the polymer alloy melt was filtered with a metal non-woven fabric having an ultrafiltration size of 15 μm, and was melt-spun through a spinneret at a spinneret surface temperature of 215° C. at a spinning rate of 3500 m/min. Thereupon, as the spinneret, a spinneret having a spinneret pore diameter of 0.3 mm and a discharge pore length of 0.55 mm was used, but little Barus phenomenon was observed. A discharge amount per single pore at that time was 0.94 g/min. Further, a distance from a spinneret underside to a cooling initiation point (upper end of chimney) was 9 cm.

The discharged filament was cooled and solidified with the cooling air at 20° C. over 1 m, fed an oil with an oil feeding guide disposed 1.8 m below the spinneret, and wound via non-heated first draw-off roll and second draw-off roll. Thereafter, the filament was drawing-heat-treated with a first hot roller at a temperature 90° C. and a second hot roller at temperature 130° C. Thereupon, a drawing rate between the first hot roller and the second hot roller was set to be 1.5 times. The resulting polymer alloy fiber exhibited excellent properties of 62 dtex, 36 filaments, a strength of 3.4 cN/dtex, elongation of 38%, and U %=0.7%. In addition, when a cross section of the resulting polymer alloy fiber was observed with TEM, an island-in-sea structure in which poly-L-lactic acid is a sea and N6 is an island was shown, a number mean diameter of the island N6 was 55 nm, and a polymer alloy fiber which is a precursor of a N6 nano-fiber in which N6 is uniformly dispersed, was obtained.

The resulting polymer alloy fiber was immersed in a 5% aqueous sodium hydroxide solution at 95° C. for 1 hour, thereby, 99% or more of the poly-L-lactic acid component in the polymer alloy fiber was hydrolyzed and removed, and this was neutralized with acetic acid, washed with water, and dried to obtain a fiber bundle of a N6 nano-fiber. This fiber bundle was analyzed from a TEM photograph. As a result, a number mean diameter of the N6 nano-fiber was small as being 60 nm, and a constitutional ratio of single fibers having a diameter not smaller than 100 nm was 0% by weight.

The resulting fiber bundle of a N6 nano-fiber was cut into a 2 mm length to obtain a cut fiber of a N6 nano-fiber. Into a TAPPI STANDARD Niagara beater (manufactured by Toyo Seiki Seisaku-sho, Ltd.) were placed 23 L of water and 30 g of the previously obtained cut fiber; this was pre-refined for 5 minutes, and thereafter extra water was removed to recover a fiber. A weight of this fiber was 250 g, and a water contend thereof was 88% by weight. Into an automatic PFI mill (manufactured by KUMAGAI RIKI KOGYO., LTD.) was placed 250 g of the fiber in the hydrous state as it was, and this was refined for 6 minutes at a rotation number of 1500 rpm and a clearance of 0.2 mm. Into an Oster blender (manufactured by Oster) were placed 42 g of the refined fiber, 0.5 g of Sharol (registered trademark) AN-103P (manufactured by Dai-ichi Kogyo Seiyaku Co., Ltd.: molecular weight 10000) which is an anionic dispersant as a dispersant, and 500 g of water, and the mixture was stirred at a rotation number of 13900 rpm for 30 minutes to obtain a dispersion 1 having a content of a N6 nano-fiber of 1.0% by weight.

Production Example 2 of Dispersion

According to the same manner as that of Production Example 1 of dispersion except that N6 of Production Example 1 of dispersion was changed to N6 (45 weight %) having a melt viscosity of 212 Pa·s (262° C. shearing rate 121.6 sec$^{-1}$), and a melting point of 220° C., melt kneading was performed to obtain a polymer alloy chip. Then, this was melt-spun and drawing-heat-treated as in Production Example 1 of dispersion to obtain a polymer alloy fiber. The resulting alloy fiber exhibited excellent properties of 67 dtex, 36 filaments, a strength of 3.6 cN/dtex, elongation of 40%, and U %=0.7%. In addition, when a cross section of the resulting polymer alloy fiber was observed with TEM, an island in sea structure in which poly-L-lactic acid is a sea and N6 is an island was shown as in Production Example 1 of dispersion, a number mean diameter of the island N6 was 110 nm, and a polymer alloy fiber in which N6 is uniformly dispersed was obtained.

According to the same manner as that of Production Example 1 of dispersion, the resulting polymer alloy fiber was hydrolyzed to remove 99% or more of the poly-L-lactic acid component in the polymer alloy fiber, neutralized with acetic acid, washed water, and dried to obtain a fiber bundle of a N6 nano-fiber. This fiber bundle was analyzed from a TEM photograph; as a result, a number mean diameter of a N6 nano-fiber was 120 nm being small which has not previously been seen, a constitutional ratio of single fibers having a diameter of greater than 500 nm was 0% by weight, and a constitutional ratio of single fibers having a diameter of greater than 200 nm was 1% by weight.

The resulting fiber bundle of a N6 nano-fiber was cut into a 2 mm length to obtain a cut fiber of a N6 nano-fiber. This was pre-refined as in Production Example 1 of dispersion to obtain a N6 nano-fiber having a water content of 88% by weight, which was further refined as in Production Example 1 of dispersion. Into an Oster blender (manufactured by Oster) were placed 21 g of the refined fiber, 0.5 g of Sharol (registered trademark) AN-103P (manufactured by Dai-ichi Kogyo Seiyaku Co., Ltd.: molecular weight 10000) which is an anionic dispersant as a dispersant, and 500 g of water, and the mixture was stirred at a rotation number of 13900 rpm for 30 minutes to obtain a dispersion 2 having a content of a N6 nano-fiber of 0.5% by weight.

Production Example 3 of Dispersion

According to the same manner as that of Production Example 2 of dispersion except that a content of a N6 nano-fiber was adjusted to 0.1% by weight by changing a fiber amount after refining without changing amounts of water and a dispersant to be placed into an Oster blender (manufactured by Oster), a dispersion 3 of a N6 nano-fiber was obtained.

Production Example 4 of Dispersion

According to the same manner as that of Production Example 1 of dispersion except that a dispersant was not used without changing amounts of water and a fiber after refining to be placed into an Oster blender (manufactured by Oster), a dispersion 4 of a N6 nano-fiber was obtained.

Production Examples 5 and 6 of Dispersion

According to the same manner as that of Production Example 1 of dispersion except that a cutting length of a N6 nano-fiber was 0.5 mm in Production Example 5 of dispersion and a cutting length of a N6 nano-fiber was 5 mm in Production Example 6, dispersions 5 and 6 of 1.0% by weight having a content of a N6 nano-fiber were obtained.

Production Example 7 of Dispersion

Using polystyrene (PS) copolymerized with 22% of PBT (polybutyrene terephthalate) and 2-ethylhexyl acrylate having a melt viscosity of 120 Pa·s (262° C., 121.6 sec$^{-1}$) and a melting point of 225° C., and using a content of PBT of 20% by weight and a kneading temperature of 240° C., the material was melted and kneaded as in Production Example 1 of dispersion to obtain a polymer alloy chip. Thereupon, a melt viscosity of copolymerized PS at 262° C. and 121.6 sec$^{-1}$ was 140 Pa·s, and a melt viscosity of copolymerized PS at 245° C. and 1216 sec$^{-1}$ was 60 Pa·s.

This polymer alloy chip was melted in a melting part at 260° C., and introduced into a spin block at a spinning temperature of 260° C. And, the polymer alloy melt was filtered with a metal non-woven fabric having an ultrafiltration size of 15 μm, and melt-spun through a spinneret at a spinneret surface temperature 245° C. at a spinning rate of 1200 m/min as in Production Example 1 of dispersion. Thereupon, as the spinneret, a spinneret equipped with a metering part of a diameter of 0.3 mm at a discharge pore upper part, and having a discharge pore diameter of 0.7 mm, and a discharge pore length of 1.85 mm was used. Thereupon, a discharge amount per single pore was 1.0 g/min. Other various conditions such as cooling and oil feeding were the same as those of Production Example 1 of dispersion. As a result, spinnability was better, and a yarn was broken once during 1 t spinning.

The resulting undrawn yarn was drawing-heat-treated at a temperature of a first hot roller of 100° C. and a temperature of a second hot roller of 115° C. as in Production Example 1 dispersion. A drawing rate between the first hot roller and the second hot roller was set to be 2.49 times. The resulting polymer alloy fiber was 161 dtex and 36 filaments, and had a strength of 1.4 cN/dtex, elongation 33%, and U %=2.0%. In addition, when a cross section of the resulting polymer alloy fiber was observed with TEM, an island-in-sea structure in which copolymerized PS is a sea and PBT is an island was shown, a number mean diameter of PBT was 70 nm, and a polymer alloy fiber in which PBT was a nano-size, and dispersed uniformly was obtained.

The resulting polymer alloy fiber was immersed in trichloroethylene, thereby, 99% or more of copolymerized PS which is a sea component was dissolved out, and this was dried to obtain a fiber bundle of a PBT nano-fiber. This fiber bundle was analyzed from a TEM photograph; as a result, a number mean diameter of the PBT nano-fiber was small as being 85 nm, a constitutional ratio of single fibers having a diameter of greater than 200 nm was 0% by weight, and a ratio of single fibers having a diameter of greater than 100 nm was 1% by weight.

The resulting fiber bundle of a PBT nano-fiber was cut into a 2 mm length to obtain a cut fiber of a PBT nano-fiber. This was pre-refined as in Production Example 1 of dispersion to obtain a PBT nano-fiber having a water content of 80% by weight, and was refined as in Production Example 1 of dispersion. Subsequently, 25 g of this refined fiber, 0.5 g of Neugen (registered trademark) EA-87 (manufactured by Dai-ichi Kogyo Seiyaku Co., Ltd.: molecular weight 10000) which is a nonionic dispersant as a dispersant, and 500 g of water were placed into an Oster blender (manufactured by Oster); the mixture was stirred at a rotation number of 13900 rpm for 30 minutes to obtain a dispersion 7 having a content of a PBT nano-fiber of 1.0% by weight.

Production Example 8 of Dispersion

PTT (polytrimethylene terephthalate) having a melt viscosity of 220 Pa·s (262° C., 121.6 sec$^{-1}$) and a melting point of 225° C., and copolymerized PS (polystyrene) manufactured by NIPPON STEEL CHEMICAL CO., LTD. ("Estyrene" KS-18, methyl methacrylate copolymerization, melt viscosity, 110 Pa·s, 262° C., 121.6 sec$^{-1}$), a content of PTT being 25% by weight, were melted and kneaded as in Production Example 1 of dispersion at a kneading temperature of 240° C., to obtain a polymer alloy chip. Thereupon, a melt viscosity of copolymerized PS at 245° C. and 1216 sec$^{-1}$ was 76 Pa·s.

This polymer alloy chip was melted in a melting part at 260° C., and introduced into a spin block at a spinning temperature of 260° C. Then, the polymer alloy melt was filtered with a metal non-woven fabric having an ultrafiltration size of 15 μm, and melt-spun through a spinneret at a spinneret surface temperature of 245° C. and at a spinning rate of 1200 m/min as in Production Example 1 of dispersion. Thereupon, as the spinneret, a spinneret equipped with a metering part of a diameter of 0.23 mm at a discharge pore upper part, and having a discharge pore diameter of 2 mm and a discharge pore length of 3 mm was used. Thereupon, a single pore discharge amount was 1.0 g/min. Other various conditions such as cooling and oil feeding were the same as those of Production Example 1 of dispersion. As a result, spinnability was better, and a yarn was broken once during 1 t spinning.

The resulting undrawn yarn was drawn 2.6 times in a warm water bath at 90° C. The resulting polymer alloy fiber was 3.9 dtex and 36 filaments, and had a strength of 1.3 cN/dtex and elongation of 25%. In addition, when a cross section of the resulting polymer alloy fiber was observed with TEM, an island-in-sea structure in which copolymerized PS is a sea and PDT is an island was shown, a number mean diameter of PTT was 75 nm, and a polymer alloy fiber in which PTT is a nano-size and is uniformly dispersed, was obtained.

Subsequently, as in Production Example 7 of dispersion, 99% or more of the copolymerized PS component in the polymer alloy fiber was dissolved out, and dried to obtain a fiber bundle of a PTT nano-fiber. This fiber bundle was analyzed from a TEM photograph and, as a result, a number mean diameter of the PTT nano-fiber was small as being 95 nm, a constitutional ratio of single fibers having a diameter of greater than 200 nm was 0% by weight, and a constitutional ratio of single fibers having a diameter of greater than 100 nm was 3% by weight.

The resulting fiber bundle of a PTT nano-fiber was cut into a 2 mm length to obtain a cut fiber of the PTT nano-fiber. This was pre-refined as in Production Example 1 of dispersion to obtain a PTT nano-fiber having a water content of 80% by weight, and this was further refined as in Production Example 1 of dispersion. Into an Oster blender (manufactured by Oster) were placed 25 g of this refined fiber, 0.5 g of Neugen (registered trademark) EA-87 (manufactured by Dai-ichi Kogyo Seiyaku Co., Ltd.: molecular weight 10000) which is a nonionic dispersant as a dispersant, and 500 g of water, and the mixture was stirred at a rotation number of 13900 rpm for 30 minutes to obtain a dispersion 8 having a content of a PTT nano-fiber of 1.0% by weight.

Production Example 9 of Dispersion

According to the same manner as that of Production Example 1 of dispersion except that N6 was changed to PP (polypropylene)(23 weight %) having a melt viscosity of 350 Pa·s (220° C., 121.6 sec$^{-1}$) and a melting point of 162° C., the material was melted and kneaded to obtain a polymer alloy chip. A melt viscosity of poly-L-lactic acid at 220° C. and 121.6 sec$^{-1}$ was 107 Pa·s.

This polymer alloy chip was melted at a melting part at 230° C., and introduced into a spin block at a spinning temperature of 230° C. Then, the polymer alloy melt was filtered through a metal non-woven fabric having an ultrafiltration size of 15 μm, and melt-spun through a spinneret at a spinneret surface temperature of 215° C. at a spinning rate of 900 m/min as in Production Example 1 of dispersion. Thereupon, as the spinneret, the same spinneret as that of Production Example 1 of dispersion was used. Moreover, thereupon, a discharge amount per single pore was 1.5 g/min. Various conditions such as cooling and oil feeding were the same as those of Production Example 1 of dispersion.

The resulting undrawn yarn was drawing-heat-treated as in Production Example 1 of dispersion at a temperature of a first hot roller of 90° C., a temperature of a second hot roller of 130° C. and a drawing rate of 2.7 times. The resulting polymer alloy fiber was 77 dtex and 36 filaments, and had a strength of 2.5 cN/dtex and elongation of 50%. In addition, when a cross section of the resulting polymer alloy fiber was observed with TEM, an island-in-sea structure in which poly-L-lactic acid is a sea and PP is an island was shown, a number of mean diameter of PP was 235 nm, and a polymer alloy fiber in which PP is a nano-size and is uniformly dispersed was obtained.

The resulting polymer alloy fiber was immersed in a 5% aqueous sodium hydroxide solution at 98° C. for 1 hour, thereby, 99% or more of the poly-L-lactic acid component in the polymer alloy fiber was hydrolyzed and removed, and this was neutralized with acetic acid, washed with water, and dried to obtain a fiber bundle of a PP nano-fiber. This fiber bundle was analyzed from a TEM photograph and, as a result, a number mean diameter of the PP nano-fiber was 240 nm, and a ratio of single fibers having a diameter of greater than 500 nm was 0% by weight The resulting fiber bundle of a PP nano-fiber was cut into a 2 mm length to obtain a cut fiber of the PP nano-fiber. This was pre-refined as in Production Example 1 of dispersion to obtain a PP nano-fiber having a water content of 75% by weight, and this was further refined as in Production Example 1 of dispersion. Into an Oster blender (manufactured by Oster) were placed 20 g of this refined fiber, 0.5 g of Neugen (registered trademark) EA-87 (manufactured by Dai-ichi Kogyo Seiyaku Co., Ltd.: molecular weight 10000) which is a nonionic dispersant as a dispersant, and 500 g of water, and the mixture was stirred at a rotation a number of 13900 rpm for 30 minutes to obtain a dispersion 9 having a content of a PP nano-fiber of 1.0% by weight.

Production Example 10 of Dispersion

Using a double-screw extruder, 80% by weight of PET having a melt viscosity of 280 Pa·s (300° C., 1216 sec$^{-1}$), and 20% by weight of polyphenylene sulfide (PPS) having a melt viscosity of 160 Pa·s (300° C., 1216 sec$^{-1}$) were melted and kneaded under the following conditions to obtain a polymer alloy chip. Herein, as PPS, straight PPS having a molecular chain end substituted with a calcium ion was used.
Screw L/D=45
  A kneading part length is 34% of a screw effective length.
  A kneading part is dispersed throughout a screw.
  There are two places of a back flow part midway.
  Polymer supply PPS and PET were separately weighed and supplied to kneader separately.
Temperature 300° C.
Vent None
The resulting polymer alloy chip was melted in a melting part at 315° C., and introduced into a spin block at a spinning temperature of 315° C. Then, the polymer alloy melt was filtered with a metal non-woven fabric having an ultrafiltration size of 15 μm, and melt-spun through a spinneret having a spinneret surface temperature of 292° C. at a spinning a rate of 1000 m/min. Thereupon, as the spinneret, a spinneret equipped with a metering part of a diameter of 0.3 mm at a discharge pore upper part, and having a discharge pore diameter of 0.6 mm and a discharge diameter of 1.75 mm was used. Moreover, at that time, a discharge amount per single pore was 1.1 g/min. Further, a distance from a spinneret underside to a cooling initiation point was 7.5 cm.

The discharged yarn was cooled and solidified with a cooling air at 20° C. over 1 m, was fed a step lubricant containing mainly fatty acid ester, and wound by a non-heated first draw-off roll and second draw-off roll. Thereupon, spinnability was better, and a yarn was not broken during 24 hour continuous spinning. This was drawing-heat-treated at a temperature of a first hot roller of 100° C. and a temperature of a second hot roller of 130° C. Thereupon, a drawing rate between the first hot roller and the second hot roller was set to be 3.3 times. The resulting polymer alloy fiber exhibited excellent properties of 400 dtex, 240 filaments, a strength of 4.4 cN/dtex, elongation of 27%, and U %=1.3%. In addition, when a cross section of the resulting polymer alloy fiber was observed with TEM, an island-in-sea structure in which PET is a sea and PPS is an island was shown, a number mean diameter of PPS was 65 nm, and a polymer alloy fiber in which PPS is uniformly dispersed was obtained.

The resulting polymer alloy fiber was immersed in a 5% aqueous sodium hydroxide solution at 98° C. for two hours, thereby, 99% or more of the PET component in the polymer alloy fiber was hydrolyzed and removed, and this was neutralized with acetic acid, washed with water, and dried to obtain a fiber bundle of a PPS nano-fiber. This fiber bundle was analyzed from a TEM photograph and, as a result, a number mean diameter of the PPS nano-fiber was small as being 60 nm, and a ratio of single fibers having a diameter of greater than 100 nm was 0% by weight.

The resulting fiber bundle of a PPS nano-fiber was cut into a 3 mm length to obtain a cut fiber of the PPS nano-fiber. This was pre-refined as in Production Example 1 of dispersion to obtain a PPS nano-fiber having a water content of 80% by weight, and this was further refined as in Production Example 1 of dispersion. Into an Oster blender (manufactured by Oster) were placed 25 g of this refined fiber, 0.5 g of Neugen (registered trademark) EA-87 (manufactured by Dai-ichi Kogyo Seiyaku Co., Ltd.: molecular weight 10000) which is a nonionic dispersant as a dispersant, and 500 g of water, and the mixture was stirred at a rotation number of 13900 rpm for 30 minutes to obtain a dispersion 10 having a content of a PPS nano-fiber of 1.0% by weight.

Production Example 11 of Dispersion

Using 60% by weight of an alkali-soluble copolymerized polyester resin as a sea component and 40% by weight of a N6 resin as an island component, melt spinning was performed. Thereupon, a 5.3 dtex polymer-oriented composite fiber in which the island component was 100 islands (hereinafter, composite fiber) was obtained. The composite fiber was thereafter drawn at a 2.5 times rate to obtain a 2.1 dtex composite fiber. This composite fiber had a strength of 2.6 cN/dtex and elongation of 35%. Thereafter, this composite fiber was treated with an aqueous sodium hydroxide solution having a 3% concentration at 98° C. for 1 hour, thereby, 99% or more of the polyester component in the composite fiber was hydrolyzed and removed; this was neutralized with acetic acid, washed with water, and dried to obtain an ultramicrofiber of N6. When an average single yarn fineness of the resulting ultramicrofiber was analyzed from a TEM photograph, the fineness corresponded to 0.02 dtex (average fiber diameter 2 μm). The resulting N6 ultramicrofiber was cut into a 2 mm length to obtain a cut fiber, 50 g of this cut fiber, 0.5 g of Sharol (registered trademark) AN-103P (manufactured by Dai-ichi Kogyo Seiyaku Co., Ltd.: molecular weight 10000) which is an anionic dispersant as a dispersant, and 500 g of water were placed into an Oster blender (manufactured by Oster); the mixture was stirred at a rotation number of 13900 rpm for 30 minutes to obtain a dispersion 11 having a content of a N6 ultramicrofiber of 1.0% by weight.

Production Example 12 of Dispersion

After a PET fiber having a single yarn fineness of 2.2 dtex (average fiber diameter 14 μm) was obtained by a method of directly melt-spinning a single component, this was cut into a 2 mm length to obtain a cut fiber. Into an Oster blender (manufactured by Oster) were placed 50 g of this cut fiber, 0.5 g of Neugen (registered trademark) EA-87 (manufactured by Dai-ichi Kogyo Seiyaku Co., Ltd.: molecular weight 10000) which is a nonionic dispersant as a dispersant, and 500 g of water, and the mixture was stirred at a rotation number of 10000 rpm for 1 minute to obtain a dispersion 12 having a content of a PET fiber of 1.0% by weight.

Production Example 13 of Dispersion

After a PET fiber having a single yarn fineness of 10 dtex (average fiber diameter 30 w) was obtained by a method of directly melt-spinning a single component, this was cut into a 2 mm length to obtain a cut fiber. Into an Oster blender (manufactured by Oster) were placed 50 g of this cut fiber, 0.5 g of Neugen (registered trademark) EA-87 (manufactured by Dai-ichi Kogyo Seiyaku Co., Ltd.: molecular weight 10000) which is a nonionic dispersant as a dispersant, and 500 g of water, and the mixture was stirred at a rotation number of 10000 rpm for 1 minute to obtain a dispersion 13 having a content of a PET fiber of 1.0% by weight.

Production Example 14 of Dispersion

After a PET fiber having a single yarn fineness of 33 dtex (average fiber diameter 55 μm) was obtained by a method of directly melt-spinning a single component, this was cut into a 2 mm length to obtain a cut fiber. Into an Oster blender (manufactured by Oster) were placed 50 g of this cut fiber, 0.5 g of Neugen (registered trademark) EA-87 (manufactured by Dai-ichi Kogyo Seiyaku Co., Ltd.: molecular weight 10000) which is a nonionic dispersant as a dispersant, and 500 g of water, and the mixture was stirred at a rotation number of 10000 rpm for 1 minute to obtain a dispersion 14 having a content of a PET fiber of 1.0% by weight.

Production Examples 15 and 16 of Dispersion

In Production Example 15 of dispersion, the dispersion 4 was diluted with water to obtain a N6 nano-fiber dispersion 15 having a content of N6 nano-fiber of 0.5% by weight, and in Production Example 16 of dispersion, the dispersion 4 was diluted with water to obtain a dispersion 16 having a content of a N6 nano-fiber of 0.1% by weight.

Production Example 17 of Dispersion

According to the same manner as that of Production Example 7 of dispersion except that a dispersion was not used without changing an amount of water to be placed into an Oster blender (manufactured by Oster); at the same time, a fiber amount after refining was changed, thereby, a content of a PBT nano-fiber was 0.5% by weight, and a dispersion 17 of a PBT nano-fiber was obtained.

Production Example 18 of Dispersion

According to the same manner as that of Production Example 9 of dispersion except that a dispersion was not used without changing an amount of water to be placed into an Oster blender (manufactured by Oster); at the same time, a fiber amount after refining was changed, thereby, a content of a PP nano-fiber was 0.5% by weight, and a dispersion 18 of a PP nano-fiber was obtained.

Production Example 19 of Dispersion

According to the same manner as that of Production Example 11 of dispersion except that a dispersion was not used without changing an amount of water to be placed into an Oster blender (manufactured by Oster); at the same time, a fiber amount after refining was changed, thereby, a content of N6 ultramicrofiber was 0.5% by weight, and a dispersion 19 was obtained.

Production Example 20 of Dispersion

According to the same manner as that of Production Example 13 of dispersion except that a dispersion was not used without changing an amount of water to be placed into an Oster blender (manufactured by Oster); at the same time, a fiber amount after refining was changed, thereby, a content of PET fiber was 0.5% by weight, and a dispersion 20 was obtained.

Production Example 21 of Dispersion

According to the same manner as that of Production Example 14 of dispersion except that a dispersion was not used without changing an amount of water to be placed into an Oster blender (manufactured by Oster); at the same time, a fiber amount after refining was changed, thereby, a content of PET fiber was 0.5% by weight, and a dispersion 21 was obtained.

Respective dispersions produced in Production Examples explained above are summarized and shown in Table 1.

TABLE 1

| | Dispersant | Fiber constituent polymer | Number mean diameter of single yarn | Ratio of bulky single fiber | Fiber concentration (wt %) |
|---|---|---|---|---|---|
| Dispersion 1 | Sharol Al-103P | N6 | 60 nm | Fiber with diameter of greater than 100 nm 0% | 1.0 |
| Dispersion 2 | Sharol Al-103P | N6 | 120 nm | Fiber with diameter of greater than 500 nm 0% Fiber with diameter of greater than 200 nm 1% | 0.5 |
| Dispersion 3 | Sharol Al-103P | N6 | 120 nm | Fiber with diameter of greater than 500 nm 0% Fiber with diameter of greater than 200 nm 1% | 0.1 |
| Dispersion 4 | None | N6 | 60 nm | Fiber with diameter of greater than 100 nm 0% | 1.0 |
| Dispersion 5 | Sharol Al-103P | N6 | 60 nm | Fiber with diameter of greater than 100 nm 0% | 1.0 |
| Dispersion 6 | Sharol Al-103P | N6 | 60 nm | Fiber with diameter of greater than 100 nm 0% | 1.0 |
| Dispersion 7 | Neugen EA-87 | PBT | 85 nm | Fiber with diameter of greater than 200 nm 0% Fiber with diameter of greater than 100 nm 1% | 1.0 |
| Dispersion 8 | Neugen EA-87 | PTT | 95 nm | Fiber with diameter of greater than 200 nm 0% Fiber with diameter of greater than 100 nm 3% | 1.0 |
| Dispersion 9 | Neugen EA-87 | PP | 240 nm | Fiber with diameter of greater than 500 nm 0% | 1.0 |
| Dispersion 10 | Neugen EA-87 | PPS | 60 nm | Fiber with diameter of greater than 100 nm 0% | 1.0 |
| Dispersion 11 | Sharol Al-103P | N6 | 2 μm | Fiber with diameter of greater than 500 nm 100% | 1.0 |
| Dispersion 12 | Neugen EA-87 | PET | 14 μm | Fiber with diameter of greater than 500 nm 100% | 1.0 |
| Dispersion 13 | Neugen EA-87 | PET | 30 μm | Fiber with diameter of greater than 500 nm 100% | 1.0 |
| Dispersion 14 | Neugen EA-87 | PET | 55 μm | Fiber with diameter of greater than 500 nm 100% | 1.0 |
| Dispersion 15 | None | N6 | 60 nm | Fiber with diameter of greater than 100 nm 0% | 0.5 |
| Dispersion 16 | None | N6 | 60 nm | Fiber with diameter of greater than 100 nm 0% | 0.1 |
| Dispersion 17 | None | PBT | 85 nm | Fiber with diameter of greater than 200 nm 0% Fiber with diameter of greater than 100 nm 1% | 0.5 |
| Dispersion 18 | None | PP | 240 nm | Fiber with diameter of greater than 500 nm 0% | 0.5 |
| Dispersion 19 | None | N6 | 2 μm | Fiber with diameter of greater than 500 nm 100% | 0.5 |
| Dispersion 20 | None | PET | 30 μm | Fiber with diameter of greater than 500 nm 100% | 0.5 |
| Dispersion 21 | None | PET | 55 μm | Fiber with diameter of greater than 500 nm 100% | 0.5 |

Example 1

Into a PP bottle having a volume of 200 cc was placed 100 g of the dispersion 1 obtained in Production Example 1 of dispersion, this was further frozen with liquid nitrogen (−196° C.) and allowed to stand in a ultralow temperature freezer at −80° C. for 30 minutes.

The frozen sample was freezing-dried with a freezing drying machine (Freeze Dry System FreeZone 2.5) manufactured by LABCONCO at a vacuum degree of not higher than 0.1 kPa to obtain a spongelike structure.

When a fiber dispersion of the resulting spongelike structure was observed with SEM, a number mean diameter of a fiber in the spongelike structure was 60 nm, and a number mean size of a micropore formed between fibers was also very small as being 300 nm. In addition, an apparent density of the spongelike structure was very small as being 0.0125 g/cm$^3$, and a porosity was very large as being 98.5%. A SEM photograph of the spongelike structure of Example 1 is shown in FIG. 1 and FIG. 2.

Examples 2-10

Regarding Examples 2 to 10, using dispersions 2 to 10 obtained in Production Examples 2 to 10 of dispersion, freezing drying was performed as in Example 1 to obtain a spongelike structure. A number mean diameter of a fiber, a number mean size of a micropore, an apparent density, and a porosity in the spongelike structure are shown in Table 2.

Examples 11

Using the dispersion 11 of the ultramicrofiber obtained in Production Example 11 of dispersion, freezing drying was performed as in Example 1 to obtain a spongelike structure. A number mean diameter of a fiber, a number mean size of a micropore, an apparent density, and a porosity in the spongelike structure are as shown in Table 2.

Examples 12 and 13

Using the dispersion 12 obtained in Production Example 12 of dispersion in Example 12, and the dispersion 13 obtained in Production Example 13 of dispersion in Example 13, freezing drying was performed as in Example 1 to obtain a spongelike structure. A number mean diameter of a fiber, a number mean size of a micropore, an apparent density, and a porosity in the spongelike structure are as shown in Table 2.

Comparative Example 1

Using the dispersion 14 obtained in Production Example 14 of dispersion, freezing drying was performed as in Example 1, but since a number mean diameter of a single fiber was too large, dispersity of the fiber in the dispersion 14 was deteriorated and a spongelike structure as in Examples could not be obtained.

Example 14

Into a PP bottle having a volume of 200 cc was placed 100 g of the dispersion 1 obtained in Production Example 1 of dispersion, and this was dried with hot air at 50° C. to remove a dispersion medium, to obtain a spongelike structure. A number mean diameter of a fiber, a number mean size of a micropore, an apparent density, and a porosity in the spongelike structure are as shown in Table 2.

Example 15

Into a PP bottle having a volume of 200 cc was placed 100 g of the dispersion 1 obtained in Production Example 1 of dispersion, and this was vacuum-dried at room temperature and a vacuum degree of 0.1 kPa to obtain a spongelike structure. A number mean diameter of a fiber, a number mean size of a micropore, an apparent density, and a porosity in the spongelike structure are as shown in Table 2.

Examples 16 and 17

Using the spongelike structure of Example 1 in Example 16, and the spongelike structure Example 2 in Example 17, pressurized steam treatment was performed for 20 minutes under the condition of 121° C. and 103.7 kPa, respectively.

Each of the resulting spongelike structures was observed with SEM. A number mean diameter of a fiber, a number mean size of a micropore, an apparent density and a porosity in the spongelike structure are as shown in Table 2. In addition, by observation with SEM, it was confirmed that fibers are partially fused and adhered by pressurized steam treatment. Further, even when each of the heat steam-treated spongelike structures was immersed in water, the structure was not disintegrated.

Example 18

The dispersion 1 obtained in Production Example 1 of dispersion was placed into a stainless tray (size: 295 mm×231 mm×49 mm), further rapidly frozen with liquid nitrogen (−196° C.), and allowed to stand in a ultralow temperature freezer at −80° C. for 30 minutes.

The frozen sample was freezing-dried with a freezing drying machine (TF5-85TPNNNS) manufactured by TAKARA SEISAKUSHO at a vacuum degree of not higher than 0.1 kPa to obtain a spongelike structure having a thickness of around 4 mm.

A number mean diameter of a fiber, a number mean size of a micropore, an apparent density, and a porosity in the spongelike structure are as shown in Table 2. A heat conductivity of the resulting spongelike structure at a measurement temperature of 23° C. was 0.039 W/m·K, and a heat conductivity at a measurement temperature of 60° C. was 0.042 W/m·K, a heat conductivity $\lambda_0$ when extrapolated to a temperature of 0° C. from these measured values was 0.037, and it was seen that the structure exhibits excellent performance as a heat insulator.

Example 19

Using the spongelike structure obtained in Example 18, a vertival incident sound absorption rate at a frequency of 100 to 5000 Hz was measured, and it was seen that a sound absorption rate is about 90% at around 4000 Hz as shown in FIG. 3, and excellent performance as an acoustic material is exhibited.

TABLE 2

|  | | Spongelike structure | | | |
| --- | --- | --- | --- | --- | --- |
|  | Dispersion used | Number mean diameter | Number mean size of micropore | Apparent density $\rho_a$ (g/cm³) | Porosity $F_v$ (%) |
| Example 1 | Dispersion 1 | 60 nm | 300 nm | 0.0125 | 98.5 |
| Example 2 | Dispersion 2 | 120 nm | 480 nm | 0.0115 | 99.0 |
| Example 3 | Dispersion 3 | 120 nm | 620 nm | 0.0082 | 99.6 |
| Example 4 | Dispersion 4 | 60 nm | 330 nm | 0.0128 | 98.7 |
| Example 5 | Dispersion 5 | 60 nm | 290 nm | 0.0127 | 98.3 |
| Example 6 | Dispersion 6 | 60 nm | 350 nm | 0.0130 | 98.7 |
| Example 7 | Dispersion 7 | 85 nm | 425 nm | 0.0131 | 98.6 |
| Example 8 | Dispersion 8 | 95 nm | 472 nm | 0.0129 | 98.8 |
| Example 9 | Dispersion 9 | 240 nm | 840 nm | 0.0135 | 97.9 |
| Example 10 | Dispersion 10 | 60 nm | 320 nm | 0.0129 | 98.6 |
| Example 11 | Dispersion 11 | 2 μm | 30 μm | 0.0249 | 97.8 |
| Example 12 | Dispersion 12 | 14 μm | 280 μm | 0.0441 | 95.2 |
| Example 13 | Dispersion 13 | 30 μm | 520 μm | 0.0631 | 94.3 |
| Comparative Example 1 | Dispersion 14 | — | — | — | — |
| Example 14 | Dispersion 1 | 60 nm | 290 nm | 0.0384 | 83.2 |
| Example 15 | Dispersion 1 | 60 nm | 310 nm | 0.0320 | 87.3 |
| Example 16 | Dispersion 1 | 60 nm | 300 nm | 0.0125 | 98.5 |
| Example 17 | Dispersion 2 | 120 nm | 480 nm | 0.0115 | 99.0 |
| Example 18 | Dispersion 1 | 60 nm | 300 nm | 0.0125 | 98.5 |
| Example 19 | Dispersion 1 | 60 nm | 300 nm | 0.0125 | 98.5 |

Examples 20-24

Each of dispersions 4, 15, 16, 17 and 18 obtained in Production Examples 4, 15, 16, 17 and 18 of dispersion was placed into a 96-well plate (well diameter 6.4 mm) for cell culture at 100 μL per well, and allowed to stand in an ultralow temperature freezer at a temperature of −80° C. for 12 hours. The frozen sample was placed into a chamber of a freezing drying machine (FD-5N) manufactured by EYELA, and freezing-dried at a vacuum degree of not higher than 0.1 kPa to obtain a spongelike structure. Further, each of the produced spongelike structures was subjected to pressurized steam treatment under the condition of 121° C. and 103.7 kPa for 20 minutes.

Thereafter, the resulting spongelike structure was observed with SEM. A number mean diameter of a fiber, a number mean size of a micropore, a number mean size of a macropore, an apparent density and a porosity in the spongelike structure are as shown in Table 3. In addition, by observation with SEM, it was confirmed that fibers are partially fused and adhered by pressurized steam treatment.

Examples 25-27

According to the same manner as that of Example 20 except that the dispersion 15 obtained in Production Example 15 of dispersion was used, and a freezing temperature was changed to −20° C., −40° C. and −150° C., respectively, freezing drying, and pressurized steam treatment were performed to obtain a spongelike structure.

Thereafter, the resulting spongelike structure was observed with SEM. A number mean diameter of a fiber, a number mean size of a micropore, a number mean size of a macropore, an apparent density and a porosity in the spongelike structure are shown in Table 3. In addition, a SEM photograph of the spongelike structure obtained in Example 26 is shown in FIG. 4.

TABLE 3

| | | | Spongelike structure | | | |
|---|---|---|---|---|---|---|
| | Dispersion used | Freezing condition | Number mean diameter | Number mean size of micropore | Number mean size of macropore | Apparent density $\rho_a$ (g/cm³) | Porosity $F_v$ (%) |
| Example 20 | Dispersion 4 | −80° C. | 60 nm | 390 nm | 62 μm | 0.0128 | 98.5 |
| Example 21 | Dispersion 15 | −80° C. | 60 nm | 420 nm | 95 μm | 0.0105 | 99.0 |
| Example 22 | Dispersion 16 | −80° C. | 60 nm | 680 nm | 220 μm | 0.0062 | 99.6 |
| Example 23 | Dispersion 17 | −80° C. | 85 nm | 560 nm | 130 μm | 0.0227 | 95.3 |
| Example 24 | Dispersion 18 | −80° C. | 240 nm | 890 nm | 430 μm | 0.0231 | 90.6 |
| Example 25 | Dispersion 15 | −20° C. | 60 nm | 500 nm | 380 μm | 0.0116 | 98.1 |
| Example 26 | Dispersion 15 | −40° C. | 60 nm | 470 nm | 270 μm | 0.0109 | 98.5 |
| Example 27 | Dispersion 15 | −150° C. | 60 nm | 330 nm | 25 μm | 0.0105 | 99.1 |

Example 28

The spongelike structure obtained in Example 25 as a cell scaffold material was placed in a 96-well plate for cell culture, 100 μl, of a mouse osteoblast 3T3-E1 cell suspension (cell concentration 5×10⁵/mL, 10% bovine fetal serum-added αMEM medium) was added, this was allowed to stand at a temperature of 37° C. for 1 hour, 900 μL of a phosphate buffer was added, an unadhered cell was washed to recover, and the unadhered cell was counted with hemocytometer abacus to calculate a ratio of adhered cells (cell retaining rate).

Further, 200 μL of a 10% bovine fetal serum-added αMEM medium was added, and cultivating was performed at a temperature of 37° C. for 48 hours under the 5% $CO_2$ atmosphere. After 48 hours, 250 μL of a cell lysate solution (0.2% Triton X-100, 1 mM EDTA, 10 mM Tris buffer (pH7.0)) was added, freezing at a temperature of −80° C. and thawing at room temperature was repeated 3 times, and a lysate was recovered. For the recovered lysate, in order to assess proliferation and differentiation of a cell, a cell DNA amount was measured with a Picogreen Assay kit (manufactured by Molecular Probe) to assess a cell number, and the alkaline phosphatase (AP) activity was measured with an AP Assay kit (Sigma) to assess osteoblast differentiation. Results are shown in Table 4. Assessment result of a cell number and the AP activity 48 hours after cell culture is shown as relative assessment, letting a value of Comparative Example 2 described later to be a standard (1.0).

Examples 29-31

According to the same manner as that of Example 28 except that, as the cell scaffold material, the spongelike structure obtained in Example 26, the spongelike structure obtained in Example 21 and the spongelike structure obtained in Example 27 were used, respectively, a cell retaining rate, and a cell number and osteoblast differentiation 48 hours after cell culture were assessed. Results are shown in Table 4.

Comparative Example 2

According to the same manner as that of Example 28 except that the spongelike structure was not used, and a 96-well plate for cell culture as a blank was used, a cell retaining rate, and a cell number and osteoblast differentiation 48 hours after cell culture were assessed. Results are shown in Table 4.

TABLE 4

| | | | Spongelike structure | | | | |
|---|---|---|---|---|---|---|---|
| | Dispersion used | Freezing condition | Number mean diameter | Number mean size of micropore | Number mean size of macropore | Apparent density $\rho_a$ (g/cm³) | Porosity $F_v$ (%) |
| Example 28 | Example 25 | 60 nm | −20° C. | 500 nm | 380 μm | 0.0116 | 98.1 |
| Example 29 | Example 26 | 60 nm | −40° C. | 470 nm | 270 μm | 0.0109 | 98.5 |
| Example 30 | Example 21 | 60 nm | −80° C. | 420 nm | 95 μm | 0.0105 | 99.0 |
| Example 31 | Example 27 | 60 nm | −150° C. | 330 nm | 25 μm | 0.0105 | 99.1 |
| Comparative Example 2 | | | A cell was cultivated in a well as a blank without using the structure. | | | | |

TABLE 4-continued

|  | Cultivating cell | Cell retaining rate | Initial cell number | Cell number relative value after 48 hours | AP activity relative value after 48 hours |
|---|---|---|---|---|---|
| Example 28 | MC3T3-E1 | 82% | $5.0 \times 10^4$ | 4.3 | 3.6 |
| Example 29 | MC3T3-E1 | 88% | $5.0 \times 10^4$ | 5.8 | 4.5 |
| Example 30 | MC3T3-E1 | 78% | $5.0 \times 10^4$ | 4.8 | 4.4 |
| Example 31 | MC3T3-E1 | 62% | $5.0 \times 10^4$ | 2.8 | 3.2 |
| Comparative Example 2 | MC3T3-E1 | 56% | $5.0 \times 10^4$ | 1.0 | 1.0 |

In Examples 28 to 31, improvement in the activity of proliferation and differentiation was confirmed.

Example 32, Comparative Example 3

A cell scaffold material in which the spongelike structure obtained in Example 26 was disposed in a 96-well plate for cell culture and a 96-well plate for cell culture as a blank were prepared, 100 μL of a phosphate buffer containing 10 ng/mL of basic fibroblast growth factor (bFGF) was added to each of them, and this was allowed to stand at a temperature 37° C. for 1 hour to adsorb bFGF thereon. After the phosphate buffer was removed, a mouse bone marrow cell (suspended in 20% bovine fetal serum-added IMDM medium) collected from a mouse (C57BL/6, female) femur was seeded on each well at $5 \times 10^3$, and cultivated for 14 days. A half of a culture medium was exchanged every two days and, after 14 days, a cell number was assessed with a cell counting kit (manufactured by Dojindo Laboratories) and, as a result, about 3 times proliferation of a cell number was confirmed as compared with a blank in the cell in which the spongelike structure was disposed.

Example 33

A 1 cm×1 cm×0.2 cm cuboid was excised from the spongelike structure obtained from Example 25, and this was immersed in 1 mL of a phosphate buffer containing 100 μg bFGF at a temperature of 37° C. overnight to prepare a cell scaffold material for regenerating a biological tissue in which bFGF was adsorbed on a surface of this spongelike structure. This cell scaffold material for regenerating a biological tissue was embedded in a back of a ddY mouse (7 week old, female) subcutaneously, and a mouse was sacrificed after 1 week. A tissue species was stained with hematoxylin eosin, and observed with a microscope, and it was confirmed that newborn blood vessel was uniformly induced in the cell scaffold material containing bFGF.

Example 34

The dispersion 1 obtained in Production Example 1 of dispersion was used and, as a dryer, Model SD10 spray dryer manufactured by Suntech Co. Ltd. was used. This dispersion 1 was added dropwise to a disk of a diameter of 5 cm which was rotating at 9000 rpm, at a rate of 20 g/min, a misty liquid droplet having a diameter of about 100 μm was sprayed under the atmosphere of 180° C. to perform drying (spray drying) and the powder was recovered.

When the resulting powder was observed with SEM, a number mean diameter of a constituent fiber was 60 nm, and a number mean size of the powder was 25 μm. A SEM photograph of the powder obtained in Example 34 is shown in FIG. 5 and FIG. 6.

When the resulting powder was coated on a hand, there was substantial feeling, and moisture retaining property was excellent. In addition, the effect of concealing a wrinkle on a coated skin was recognized.

Results are shown in Table 5.

Examples 35-43

According to the same manner as that of Example 34 except that dispersions 2 to 10 obtained in Production Examples 2 to 10 of dispersion were used, spray drying was performed to obtain a powder. A number mean diameter of a constituent fiber and a number mean size of a powder in a resulting powder are as shown in Table 5.

Comparative Example 4

According to the same manner as that of Example 34 except that the dispersion 11 obtained in Production Example 11 of dispersion was used, spray drying was performed, but a fiber became cotton-like and a powder was not obtained.

Example 44

The powder obtained in Example 34 was subjected to pressurized steam treatment for 20 minutes under the condition of 121° C. and 103.7 kPa. A number mean diameter of a constituent fiber and a number mean size of a powder in the resulting powder are as shown in Table 5.

In addition, by observation with SEM, it was confirmed that fibers are partially fused and adhered by pressurized steam treatment. Further, even when the heat steam-treated powder was immersed in water, the structures was not disintegrated.

TABLE 5

|  | Dispersion used | Powder | |
|---|---|---|---|
|  |  | Number mean diameter | Number mean size (μm) |
| Example 34 | Dispersion 1 | 60 nm | 25 |
| Example 35 | Dispersion 2 | 120 nm | 30 |
| Example 36 | Dispersion 3 | 120 nm | 20 |
| Example 37 | Dispersion 4 | 60 nm | 30 |
| Example 38 | Dispersion 5 | 60 nm | 23 |
| Example 39 | Dispersion 6 | 60 nm | 28 |
| Example 40 | Dispersion 7 | 85 nm | 32 |
| Example 41 | Dispersion 8 | 95 nm | 35 |

TABLE 5-continued

| | Dispersion used | Powder | |
|---|---|---|---|
| | | Number mean diameter | Number mean size (μm) |
| Example 42 | Dispersion 9 | 240 nm | 70 |
| Example 43 | Dispersion 10 | 60 nm | 45 |
| Comparative Example 4 | Dispersion 11 | — | — |
| Example 44 | Dispersion 1 | 60 nm | 25 |

Example 45

The powder produced in Example 44 and a commercially available lotion (The • Skin Care Hydrobalancing Softner (trade name) manufactured by Shiseido Co. Ltd.,) were mixed with a labo-stirrer for 3 minutes at the following blending ratio, to produce a lotion with a powder blended therein. Ten panelists performed organoleptical assessment when a lotion was used, and all panelists stated that there is no uncomfortable feeling at use, and there is natural feeling. In addition, by blending a powder, flowing of a cosmetic by sweat could be prevented, and cosmetic retention was improved. In addition, since a powder itself had high water retention, moisture retaining property became better by blending the powder, and moist feeling of a skin after use of a cosmetic was improved.

| Powder of Example 44 | 10 wt % |
|---|---|
| The • Skin Care Hydrobalancing Softner | 90 wt % |
| Total | 100 wt % |

Example 46

Under the condition of 120 rpm, 30 g of the powder obtained in Example 44, and 300 g of a commercially available urethane-based paint in which a solvent is toluene were stirred with a labo-kneader at 30° C. for 30 minutes to obtain a paint in which a nano-fiber was blended. Since the resulting paint had better spreading at coating with a brush, and a suitable viscosity, there was no liquid sagging, and coating processing was easy. In addition, a luster of the paint after coating was better, and a coated surface was smooth irrespective of addition of fiber.

INDUSTRIAL APPLICABILITY

The spongelike structure of the present invention is useful in industrial material utility and household wares utility such as a light reflector used in a buffering material, a water retention material and a liquid crystal in addition to a heat insulator, an acoustic material and a cell scaffold material, and is suitable in, for example, a cushioning material for vehicle interior decoration, a ceiling material, a construction material, a wiping material, a stain cleaning sheet, a health product, and a sensor member for an IT member.

In addition, the spongelike structure is suitable in filter utility, and can be utilized in from household material utility such as a mask to industrial utility such as an air filter and a liquid filter, and medical utility such as a blood filter. For example, the spongelike structure is suitable in the fields to which an air filter for a clean room, for an automobile, for ventilation of a factory and an incineration facility, and for a house, a liquid filter for a chemical process, a food, a drug and medicine, or a HEPA or ULPA filter is applied.

Further, the spongelike structure is also suitable for wiping, polishing, and abrasion, and is of course suitable in a beauty cosmetic equipment, a cleansing sheet, a skin care sheet, a medical extracorporeal, circulation column, a bandage, an adhesive skin patch.

The powder of the present invention is also suitable as a filler of a paint and a cosmetic, and a resin filler. In addition, the powder is also suitable in an adsorbent and a water retaining agent and, further, a powdery material in each field of medicine and hygiene.

BRIEF DESCRIPTION OF DRAWINGS

FIG. 1 is a SEM photograph (magnification 5000) of the spongelike structure obtained in Example 1.

FIG. 2 is a SEM photograph (magnification 5000) of the spongelike structure obtained in Example 1.

FIG. 3 is a view showing result of measurement a perpendicular incident sound absorption rate in Example 19.

FIG. 4 is a SEM photograph (magnification 300) of the spongelike structure obtained in Example 26.

FIG. 5 is a SEM photograph (magnification 500) of the powder obtained in Example 34.

FIG. 6 is a SEM photograph (magnification 2000) of the powder obtained in Example 34.

The invention claimed is:

1. A process for producing a spongelike three-dimensional structure of fibers of a synthetic polymer, comprising preparing a fiber dispersion by dispersing the fibers of the synthetic polymer, the fibers having a number mean diameter of 1 nm to 50 μm, in a dispersion media; drying the fiber dispersion; removing the dispersion media to fix the fibers in a three-dimensional dispersed state comprising randomly oriented fibers which are not substantially aggregated; and subjecting the fibers in the three-dimensional dispersed state to a pressurized steam treatment under a temperature condition of not lower than a glass transition temperature of the synthetic polymer used as a raw material of the fiber and not higher than a melting temperature of the polymer to partially fuse and adhere the fibers of the synthetic polymer and obtain the spongelike three-dimensional structure of the fibers of the synthetic polymer fixed in the dispersed state.

2. The process for producing a spongelike structure according to claim 1, wherein a number mean diameter of the fiber is 1 to 500 nm.

3. The process for producing a spongelike structure according to claim 2, wherein a fiber constituent ratio of single fibers having a diameter of more than 500 nm is not more than 3% by weight.

4. The process for manufacturing a spongelike structure according to claim 1, wherein the fiber comprises a thermoplastic polymer.

5. The process for producing a spongelike structure according to claim 1, wherein a cut fiber length of the fiber is 0.2 mm to 30 mm.

6. The process for producing a spongelike structure according to claim 1, wherein the drying is freeze drying.

7. The process for producing a spongelike structure according to claim 6, wherein a freezing temperature upon freeze drying is not lower than −80° C. and not higher than −20° C.

* * * * *